United States Patent [19]
Wyatt et al.

[11] Patent Number: 5,603,706
[45] Date of Patent: Feb. 18, 1997

[54] INFUSION APPARATUS

[76] Inventors: Philip Wyatt, 1018 Marengo Dr., Glendale, Calif. 91206; Gary Schaeffer, 50 E. Alice St. #E, Arcadia, Calif. 91006

[21] Appl. No.: 229,627

[22] Filed: Apr. 19, 1994

Related U.S. Application Data

[63] Continuation-in-part of Ser. No. 954,528, Sep. 29, 1992, Pat. No. 5,356,396.

[51] Int. Cl.⁶ ................................................. A61M 25/00
[52] U.S. Cl. .................... 604/283; 604/280; 604/284; 604/905; 137/223
[58] Field of Search ................................. 604/167, 164, 604/280, 283, 278, 256, 284, 905; 137/223

[56] References Cited

U.S. PATENT DOCUMENTS

| | | |
|---|---|---|
| 2,295,804 | 9/1942 | Olson . |
| 2,387,455 | 7/1945 | McDermott . |
| 3,100,641 | 8/1963 | Nicholls et al. . |
| 3,495,594 | 11/1966 | Swanson . |
| 5,047,021 | 9/1991 | Utterberg . |
| 5,057,093 | 10/1991 | Clegg et al. . |
| 5,188,620 | 2/1993 | Jepson et al. . |
| 5,199,620 | 2/1993 | Jepson et al. . |
| 5,203,775 | 4/1993 | Frank et al. . |
| 5,211,638 | 5/1993 | Dudar et al. . |
| 5,248,306 | 9/1993 | Clark et al. . |
| 5,290,222 | 3/1994 | Feng . |
| 5,344,414 | 9/1994 | Lopez et al. . |

*Primary Examiner*—Randall L. Green
*Assistant Examiner*—Perry E. Van Over
*Attorney, Agent, or Firm*—J. E. Brunton

[57] ABSTRACT

A family of variously configured, new, improved and universally compatible infusion sites and medical connectors that employ a cannula and which function to interconnect uniquely configured T sites, Y sites, heparin locks and the like with a liquid source, such as an I.V. source.

25 Claims, 17 Drawing Sheets

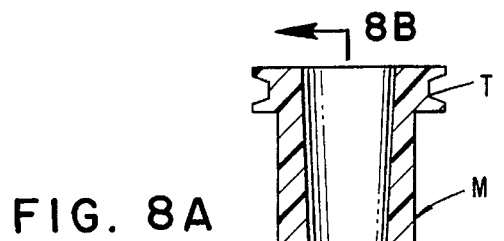
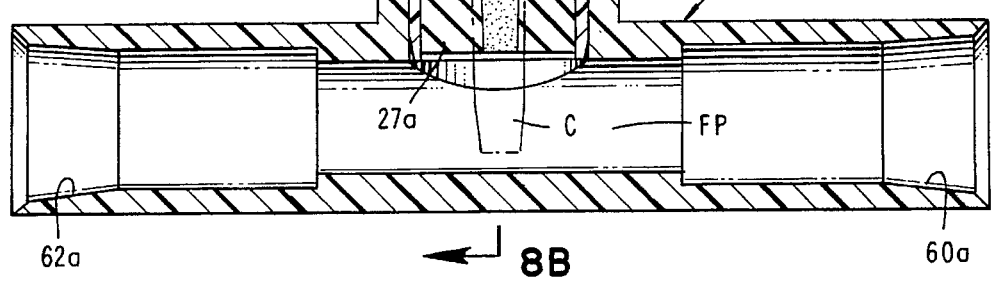
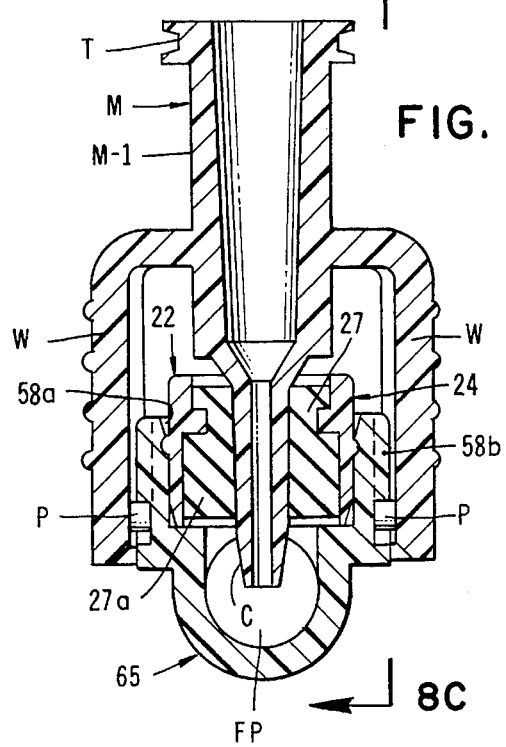
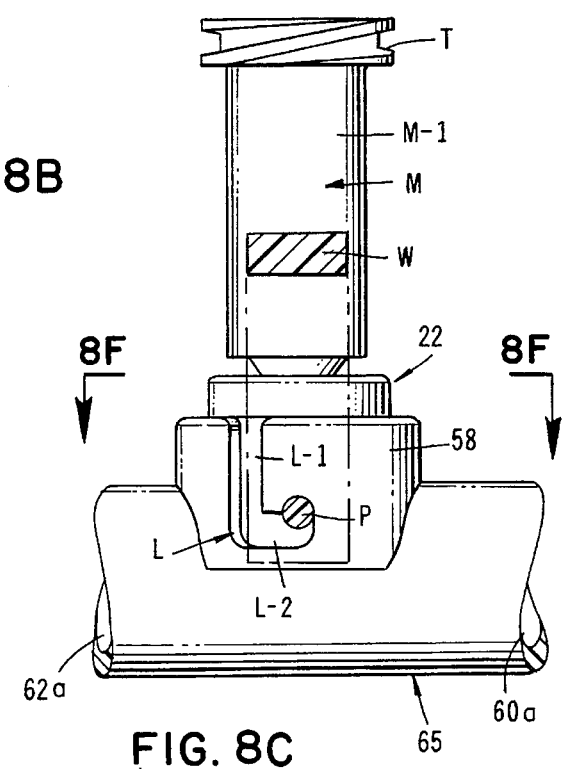

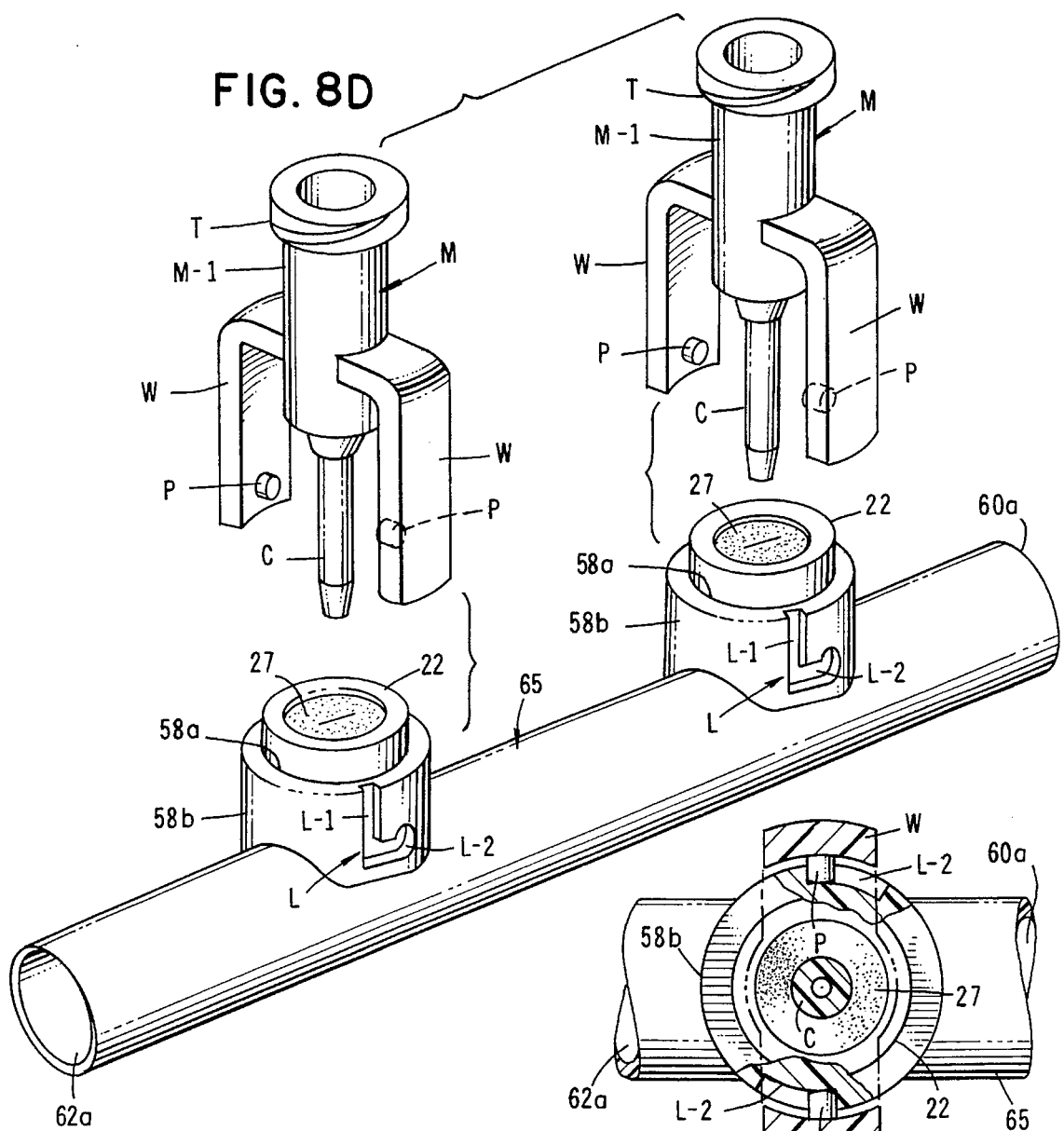
FIG. 8D
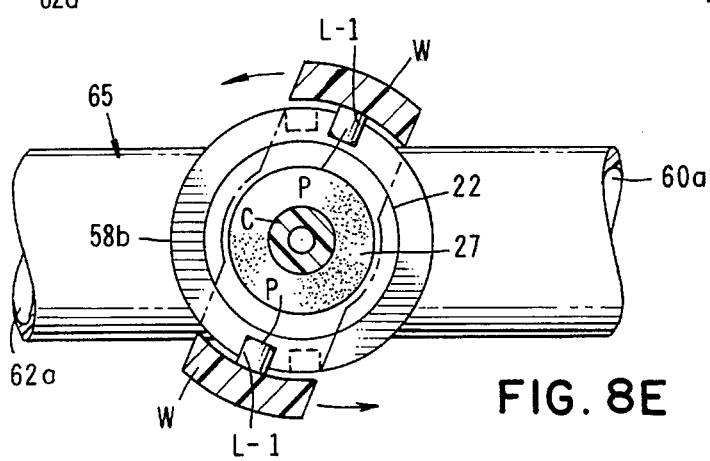
FIG. 8F
FIG. 8E

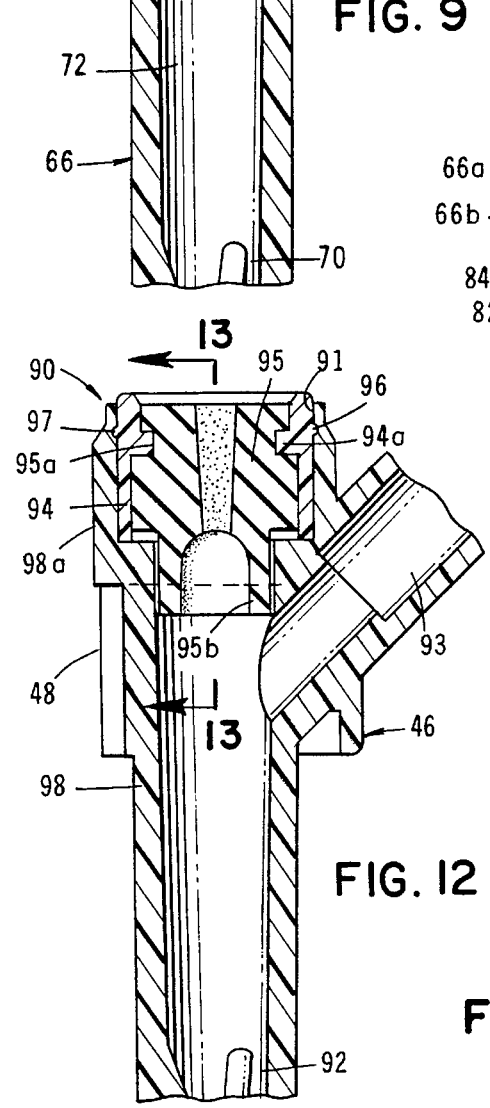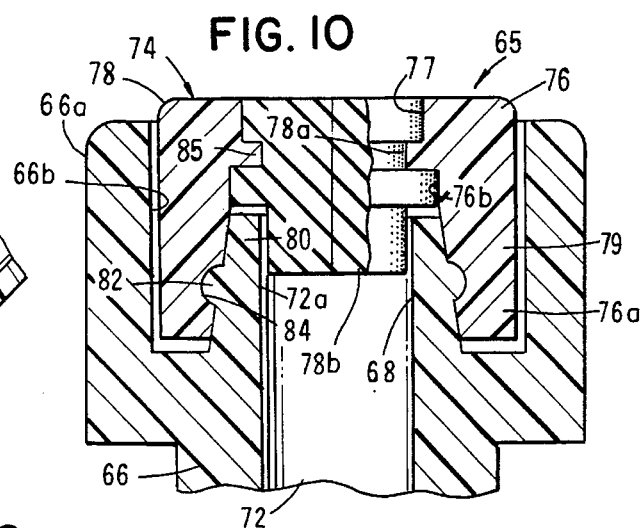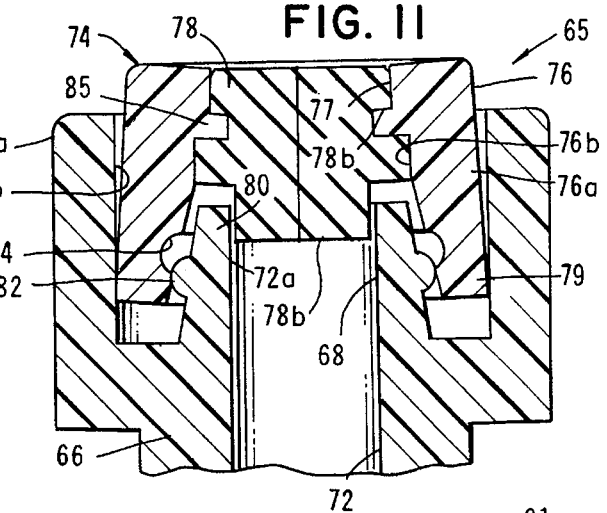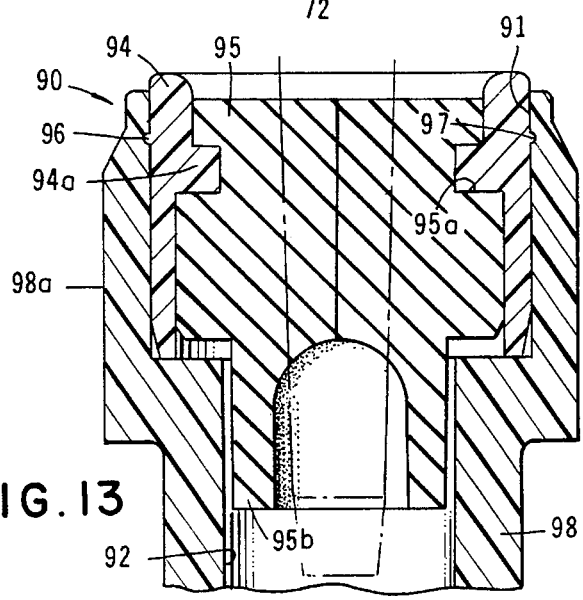

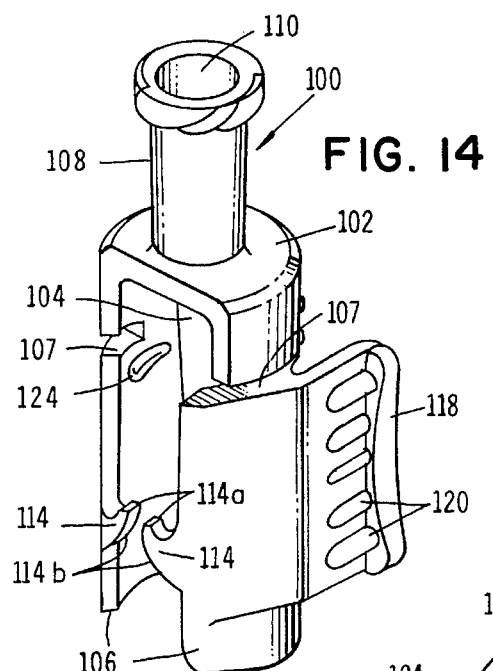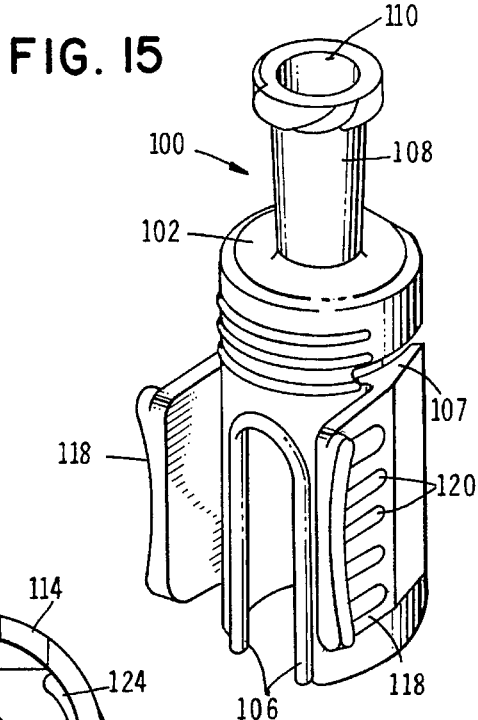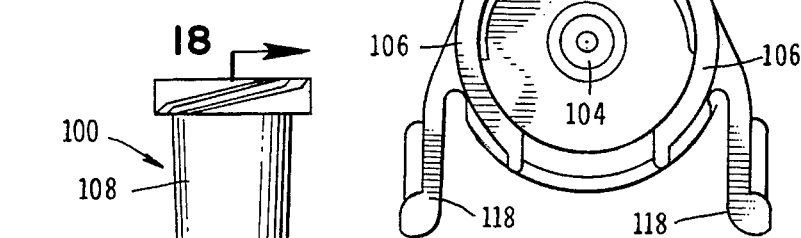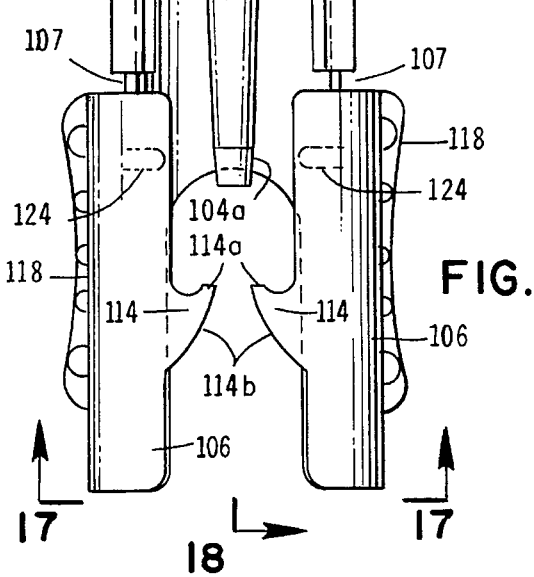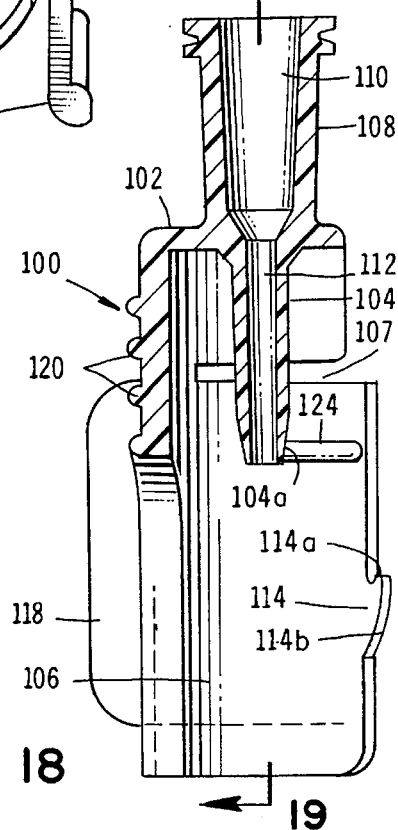

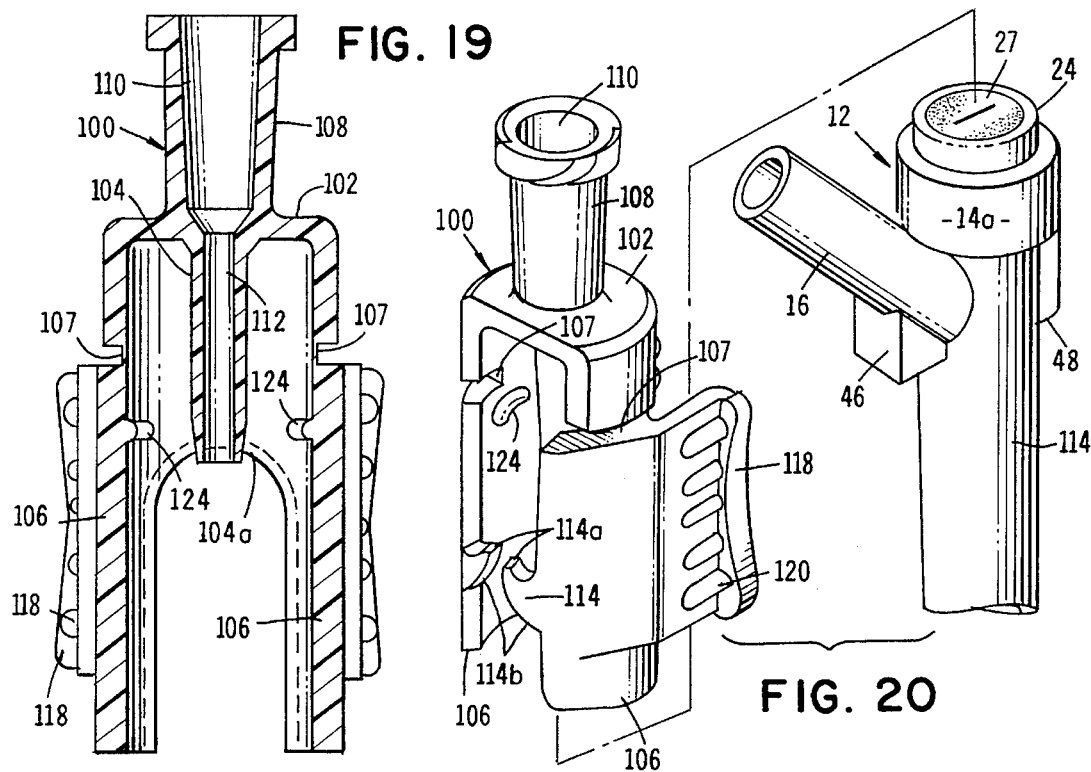
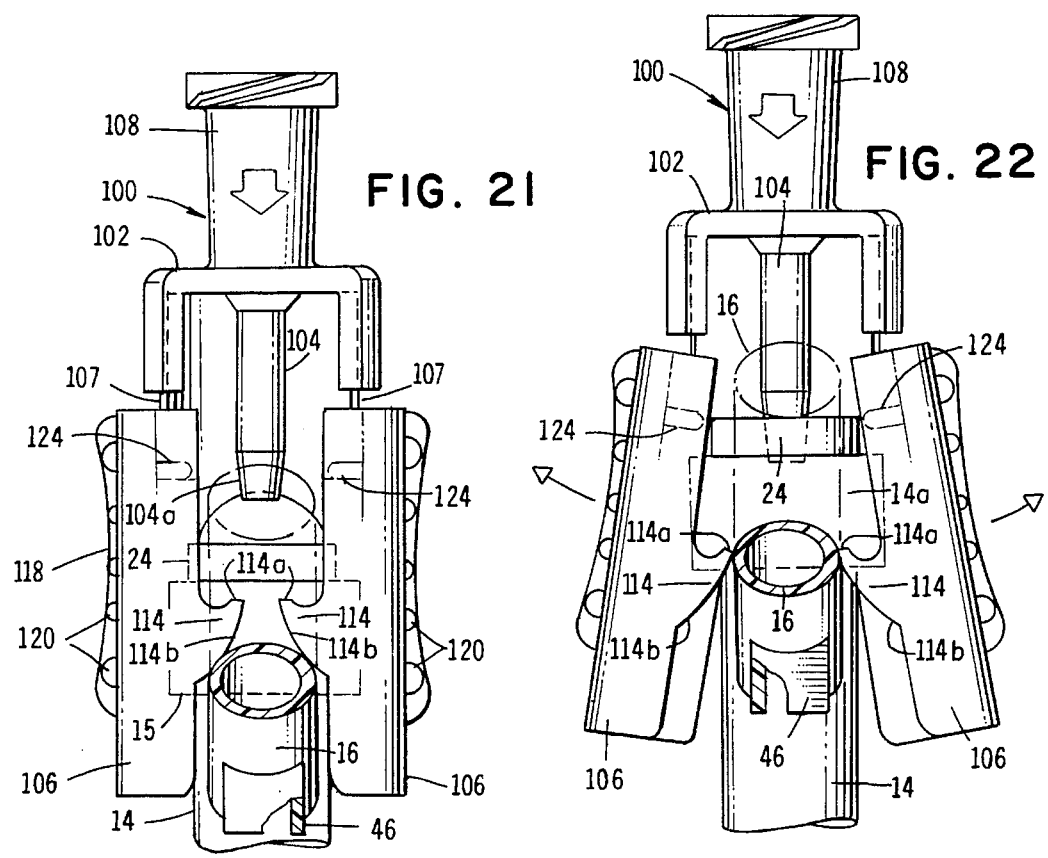

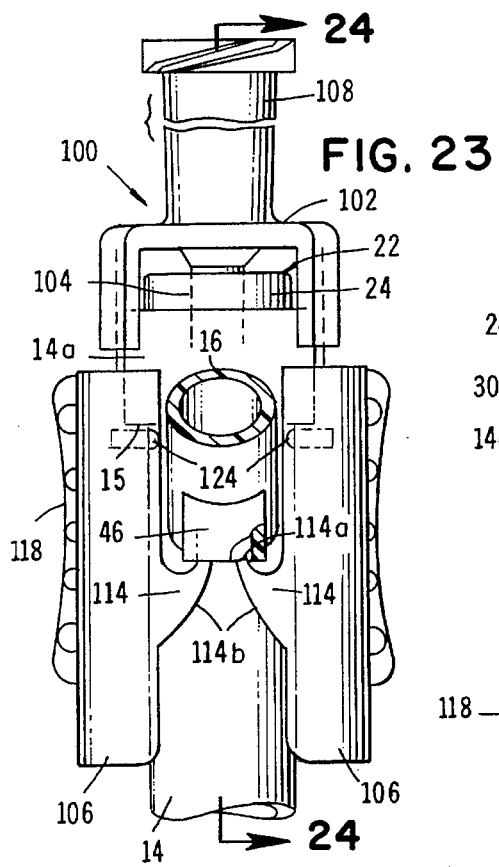
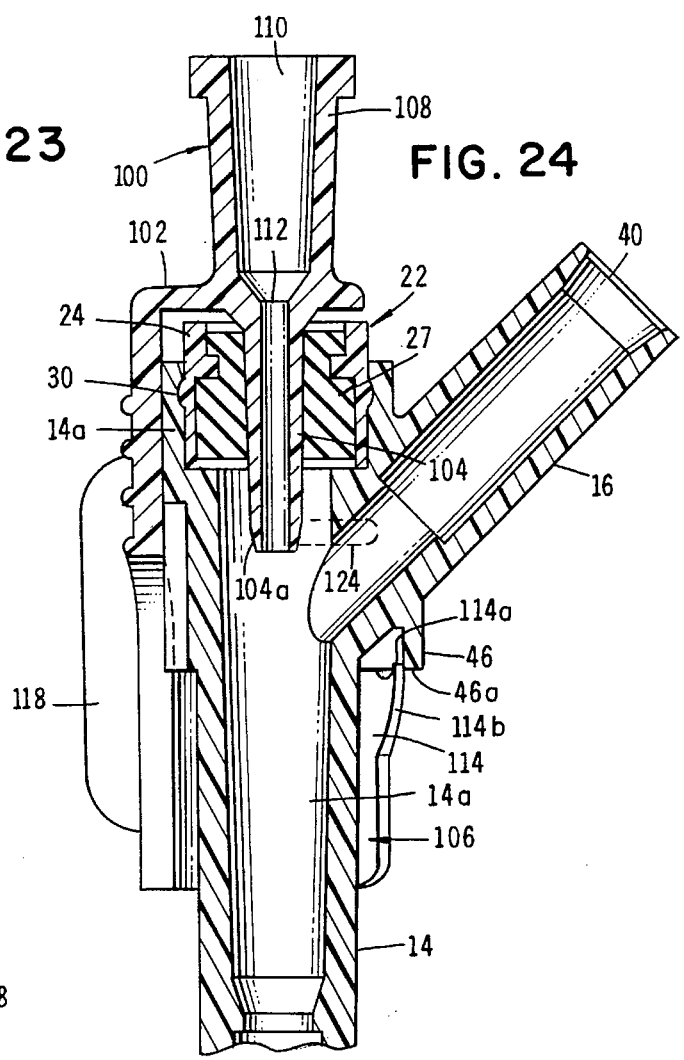
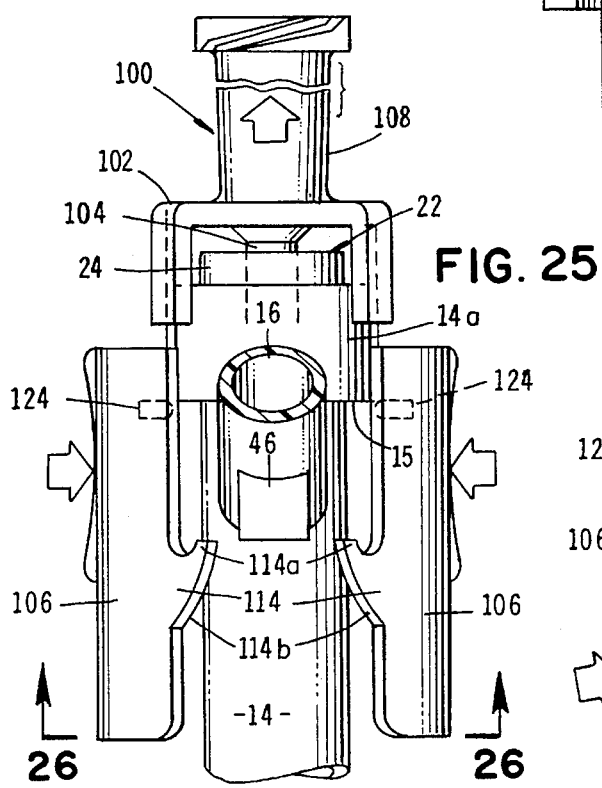
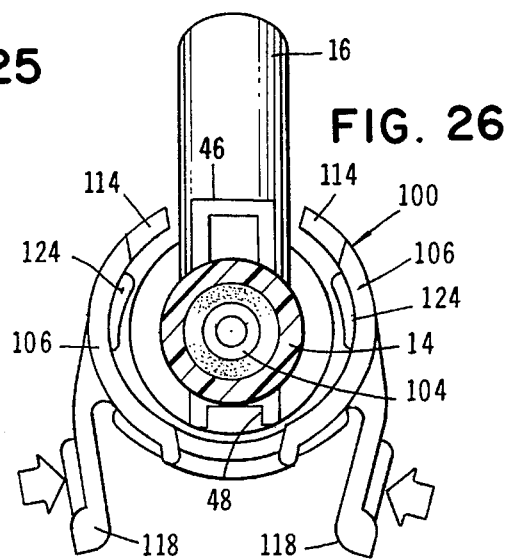

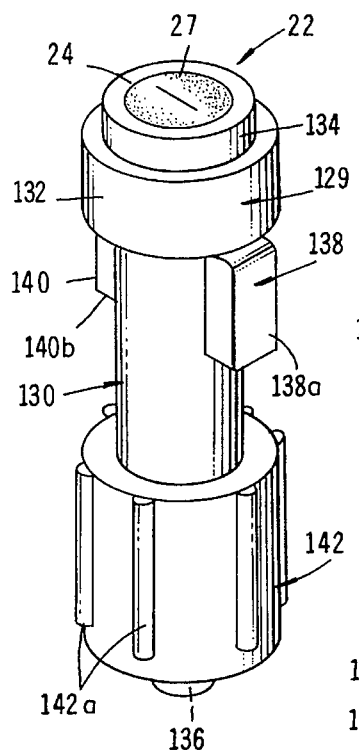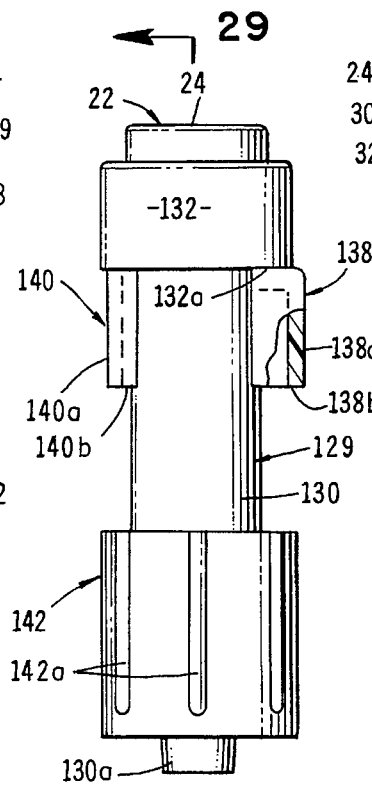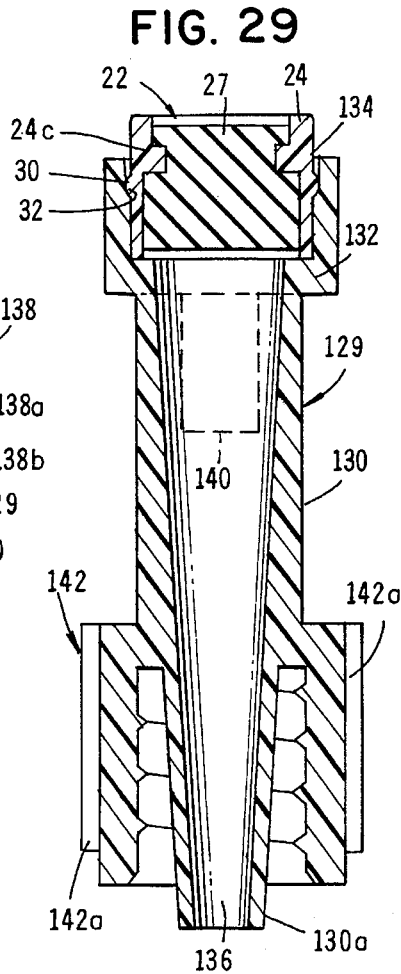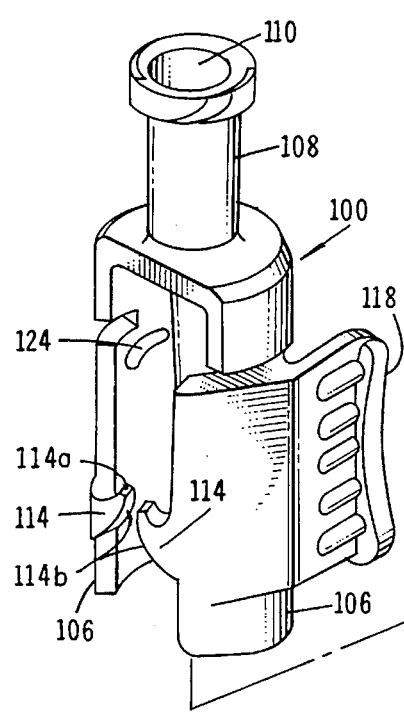
FIG. 27
FIG. 28
FIG. 29
FIG. 30

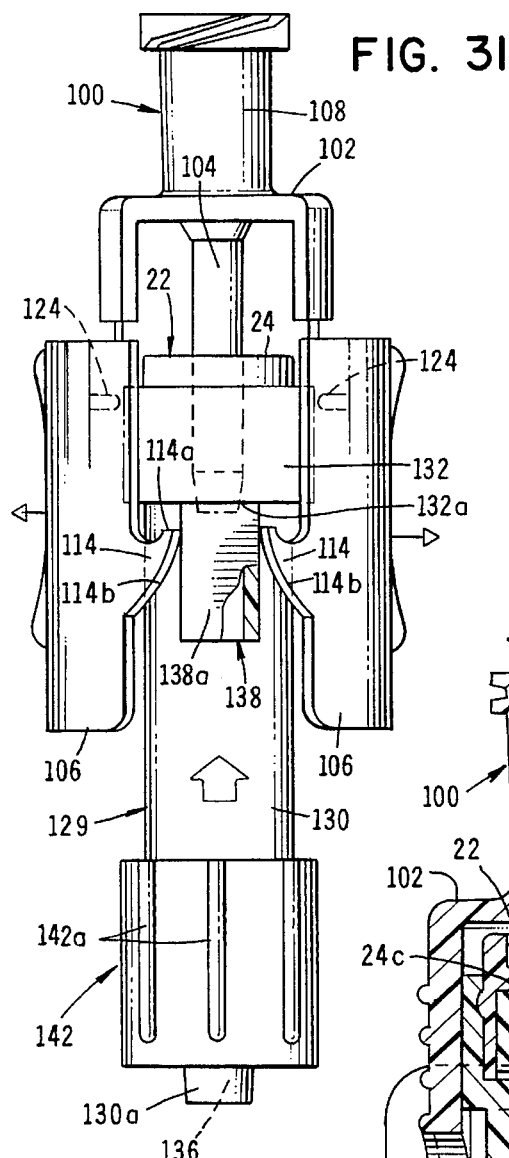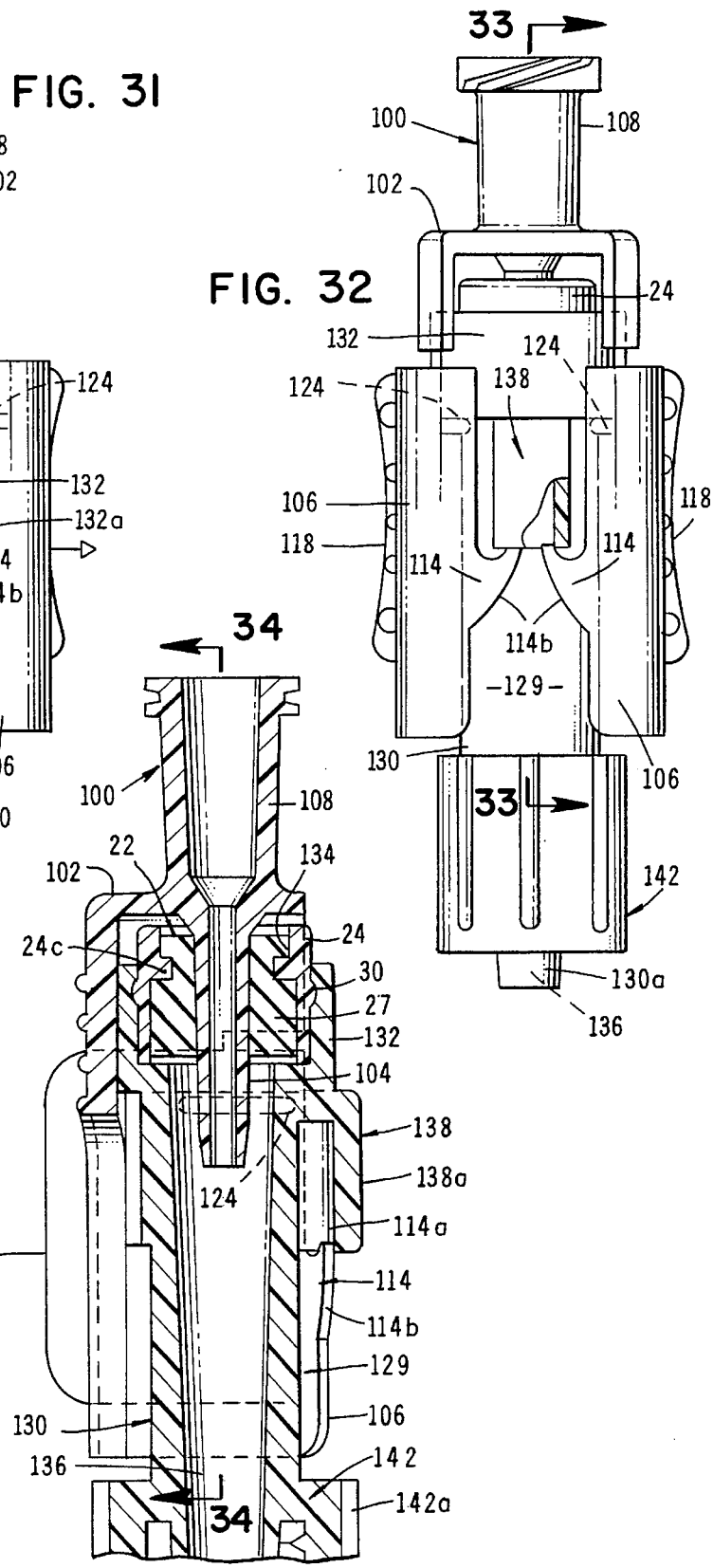

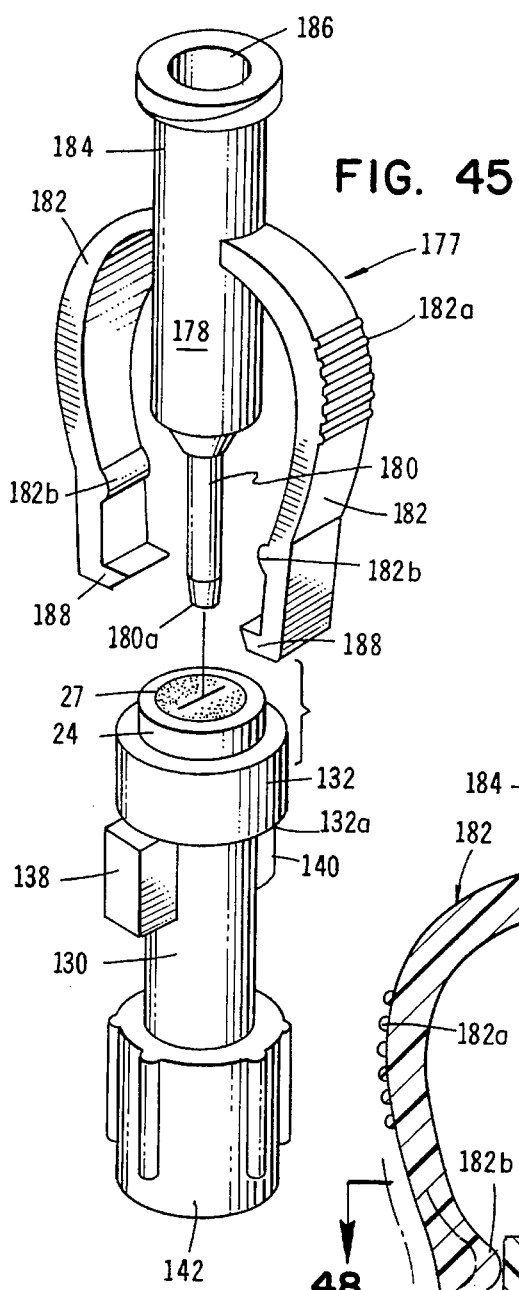
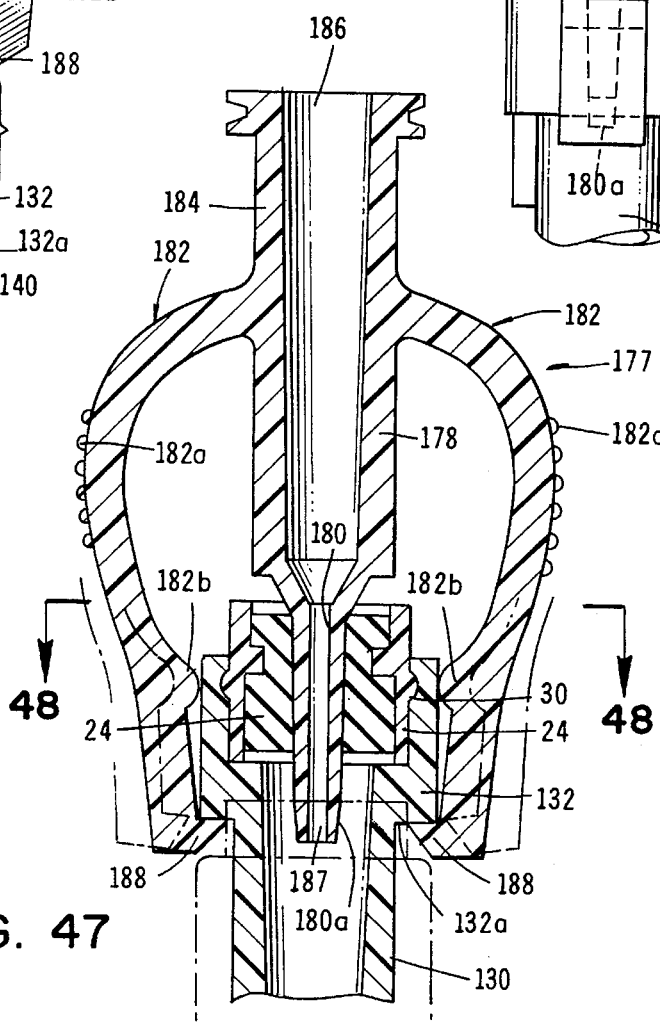
FIG. 45
FIG. 46
FIG. 47

INFUSION APPARATUS

BACKGROUND OF THE INVENTION

This is a Continuation-In-Part application of application, Ser. No. 07/954,528, filed Sep. 29, 1992, now U.S. Pat. No. 5,356,396.

1. Field of the Invention

The present invention relates generally to infusion systems, including medical connectors. More particularly, the invention concerns a family of new and improved entry port structures and cooperating medical connectors which employ a recessed cannula. The medical connectors function to interconnect both standard and specially designed entry port structures such as T sites, Y sites, heparin locks and the like with a liquid source, such as an I.V. source.

2. Discussion of the Invention

The use of the intravenous or giving sets for the administration of parenteral fluids to a patient is a common practice. In its simplest form, the intravenous set comprises a length of tubing, one end of which is provided with a fitting for making a connection with a source of parenteral fluid such as a bottle or an elevated flexible bag. The other end of the tubing is typically provided with a needle or catheter which may be inserted into the vein of the patient. Frequently it is desirable to interconnect a secondary conduit with the length of tubing to enable infusion of a second parenteral fluid, inject a medication or sample bodily fluids. This is generally accomplished through the use of an intermediate entry port structures, such as a "Y" site or "T" site unit. Both Y site and T site connector are units generally made with a straight tubular body portion and a hollow arm which extends laterally from the body portion. Typically at least one end of the body portion, as well as the open end of the arm portion, is provided with a seal of some type such as penetrable self-sealing septum adapted to accept a cannula such as the cannula of a syringe or a needle connector.

In use, the needle connector is mounted over the end of the Y or T site connector with the cannula piercing through the self-sealing septum. In the past, substantial difficulties have been encountered in designing a needle connector which can be appropriately secured in place with respect to the Y or T site connector. In some instances, in order to ensure an appropriate connection, the needle or connector has been designed to envelope the entire Y or T site connector. In other instances elaborate multi-part connectors have been designed to positively lock the needle connector to the Y or T site connector. Exemplary of this latter class of devices are those described in U.S. Pat. No. 4,998,713 issued to Vaillancourt. Many of the prior art devices, including the Vaillancourt devices, also include a protective shield of some type within which the needle is mounted. Another connector, which also provides a protected cannula, is disclosed in U.S. Pat. No. 4,834,716 issued to Ogle, II. Still another type of prior art connector is described in U.S. Pat. No. 4,964,855 issued to Todd, et al. A connector shown in U.S. Pat. No. 4,752,292 issued to Lopez, et al. discloses various types of locking mechanisms for use with non-standard, specially configured Y sites and other specially configured sealed port structures.

A principal drawback of many of the prior art connector devices is the fact that frequently the devices cannot be used with Y sites, T sites and heparin locks of standard construction. Further many of the prior art connectors cannot be securely attached even to Y or T sites of specially non-standard construction, and therefore can become relatively easily separated therefrom. If the connector separates from the entry port structure, the flow of parenteral liquids to the patient will, of course, interrupted. The result can be catastrophic, particularly if the patient is in intensive care. To avoid such separation, tape is sometimes used in an to attempt to more securely interconnect the needle connector with the standard or specially configured Y or T site. However, this approach is quite cumbersome, inconvenient and generally undesirable since the tape can also easily work loose thereby permitting the needle connector to separate from the Y or T site.

To avoid undesirable separation of the connector from the Y site, T site, or other entry port structure several complex, multi-port connector devices have been suggested. Typically, these devices are often difficult to use and are quite expensive to manufacture. Additionally, many of the devices do not have universal applicability and are usable only with particular types of Y or T sites thereby further limiting their practicability.

The thrust of the present invention is to overcome the drawbacks of the prior art by providing an easy to use, elegantly simple family of infusion devices, including low dead space infusion sites and universal connectors which provide a positive and secure connection to all commonly used Y sites, T sites and heparin locks. The devices are user friendly, highly reliable and can be inexpensively manufactured. They will accept commercially available Y sites and T sites of varying sizes and configurations and advantageously provide both tactile and audio locking features. Further, the devices provide uniquely configured cannula shrouds which effectively protect against contamination and needle stick.

Several embodiments of the invention are illustrated and described in co-pending application, Ser. No. 07/954,528, filed Sep. 29, 1992, which application is incorporated by reference herein in its entirety as if fully set forth herein.

SUMMARY OF THE INVENTION

It is an object of the present invention to provide a family of low dead space entry port structures, such as heparin locks, sampling ports and Y and T sites, which can be aseptically interconnected with a source of fluids, such as an I.V. source, using connectors, or couplers of unique design. The connectors uniquely mate with the entry port structures in a manner which positively prevents accidental separation of the connectors from the entry port structure. In this way, the accidental interruption of the flow of parenteral liquids to the patient is effectively prevented.

Another object of the invention is to provide an infusion system in which the connectors can be mated with a number of different types of commercially available, entry port structures of both standard and special construction and include extended length shrouds which function to positively prevent accidental needle stick. The connectors will accept large and small diameter Y and T sites as well as heparin locks and will accommodate Y sites having both high and low Y locations.

Another object of the invention is to provide an infusion system of the aforementioned character in which the connectors embody both tactile and audio locking features to ensure positive interconnection with the mating infusion site. The locking elements are advantageously disposed within a cylindrical boundary generally defined by the boundary of the shroud portion of the connector and extensions thereof.

Another object of the invention is to provide an infusion system as described in the preceding paragraphs in which the connector's positively resist disengagement and embody dual locking mechanisms to guard against accidental separation. Further, the connectors include specially configured mounting surfaces to enable easy interconnection of the device with the patient.

Another object of the invention is to provide a fluid sampling system in which the sampling port of the system can be mated with the various connectors of the invention.

Still another object of the invention is to provide connectors of the character described having easy-to-use and release locking mechanisms including textured release arms, grips, rotating locking collars and pen snaps.

Another object of the invention is to provide connectors of the type described in the preceding paragraphs which effectively eliminate wobbling and pistoning (and the possible contamination resulting therefrom) of the needle within the septum and which can embody both metal and plastic cannulas.

Yet another object of the invention is to provide an infusion system which includes entry port structures embodying septums of unique design that will sealably accommodate cannulas of various types and will permit repeated puncture without leaking.

Another object of the invention is to provide novel entry port structures as defined in the preceding paragraph in which uniquely configured septums are mounted within novel connector rings, which, in turn, are mounted within the upper body of the entry port structures.

Another object of the invention is to provide a family of mating infusion components of the character described which are safe and easy to use, are constructed of yieldably deformable, clear plastic materials that are compatible with most drugs and parenteral liquids and are inexpensive to manufacture in large volume.

BRIEF DESCRIPTION OF THE DRAWINGS

FIG. 8A is a cross-sectional view of yet another alternate form of injection site of the infusion apparatus of the invention showing one form of medical connector of the invention interconnected therewith.

FIG. 8B is a cross-sectional view taken along lines 8B—8B of FIG. 8A.

FIG. 8C is a view taken along lines 8C—8C of FIG. 8B.

FIG. 8D is a generally perspective exploded view of the infusion apparatus shown in FIGS. 8A, 8B, and 8C.

FIG. 8E is a cross-sectional view similar to 8F but showing the medical connector in an unlocked position.

FIG. 8F is a cross-sectional view taken along lines 8F—8F of FIG. 8C.

FIG. 9 is a cross-sectional view of still an alternate form of injection site of the infusion apparatus of the invention.

FIG. 10 is an enlarged, fragmentary, cross-sectional view taken along lines 10—10 of FIG. 9.

FIG. 11 is a cross-sectional view similar to FIG. 10, but showing the closure assembly, including the septum, being mated with the injection site housing.

FIG. 12 is a cross-sectional view of still another form of injection site of the infusion apparatus of the invention which embodies a closure assembly of slightly different configuration.

FIG. 13 is a greatly enlarged, cross-sectional view taken along lines 13—13 of FIG. 12.

FIG. 14 is a generally perspective front view of one form of medical connector of the infusion apparatus of the invention.

FIG. 15 is a generally perspective rear view of the medical connector shown in FIG. 14.

FIG. 16 is an enlarged, front-elevational view of the connector shown in FIG. 14.

FIG. 17 is a view taken along lines 17—17 of FIG. 16.

FIG. 18 is a cross-sectional view taken along lines 18—18 of FIG. 16.

FIG. 19 is a cross-sectional view taken along lines 19—19 of FIG. 18.

FIG. 20 is a generally perspective, exploded view illustrating the manner of mating the medical connector with one form of injection site of the apparatus of the invention.

FIG. 21 is a front elevational view of the components of FIG. 20 showing the components in an initial mating position.

FIG. 22 is a front elevational view similar to FIG. 21 but showing the medical connector advanced further over the injection site.

FIG. 23 is a front elevational view similar to FIG. 22 but showing the component parts in a fully mated configuration.

FIG. 24 is a cross-sectional view taken along lines 24-24 of FIG. 23.

FIG. 25 is a front elevational view similar to FIG. 23 but showing the position of the parts after a separating force has been directed upon the medical connector.

FIG. 26 is a view taken along lines 26—26 of FIG. 25.

FIG. 27 is a generally perspective view of still an another form of injection site of the infusion apparatus of the present invention.

FIG. 28 is a front view of the injection site shown in FIG. 27.

FIG. 29 is an enlarged, cross-sectional view taken along lines 29—29 of FIG. 28.

FIG. 30 is a generally perspective, exploded view of a medical connector which is mateable with the injection site of FIG. 27.

FIG. 31 is an enlarged front elevational view of the medical connector of FIG. 30 in an initial mating position with the injection site of FIG. 30.

FIG. 32 is a view similar to FIG. 31, but showing the components in a fully mated configuration.

FIG. 33 is an enlarged, cross-sectional view taken along lines 33—33 of FIG. 32.

FIG. 45 is a generally perspective, exploded view of yet another form of infusion apparatus of the present invention.

FIG. 46 is a fragmentary side view of the apparatus shown in FIG. 45.

FIG. 47 is an enlarged front elevational view of the apparatus of FIG. 45 in a mated position.

DESCRIPTION OF THE INVENTION

Figure 1:
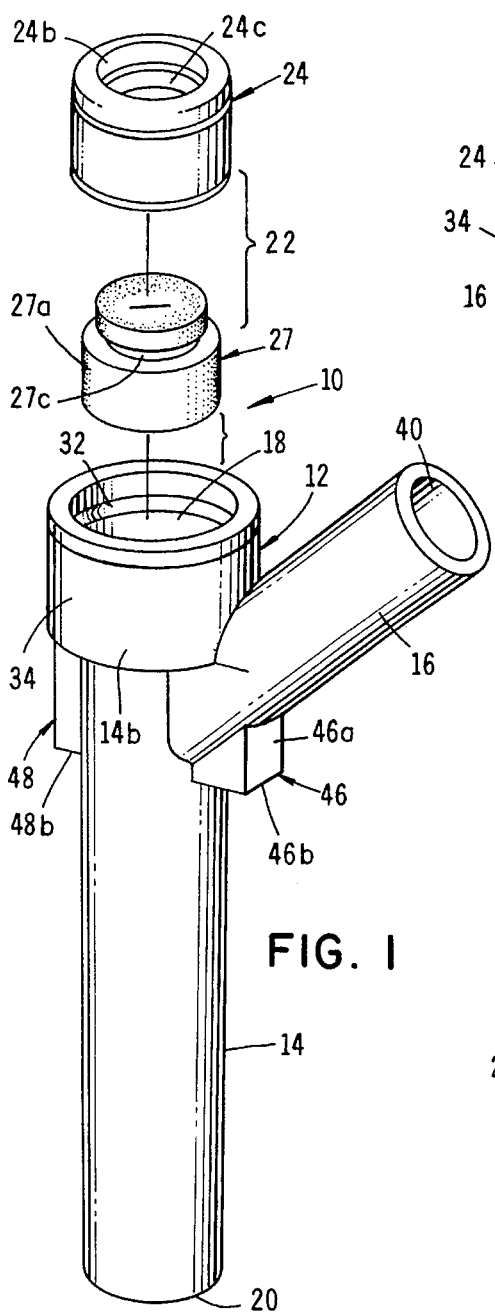
FIG. 1 is a generally perspective, exploded view of one form of the injection site of the apparatus of the invention here shown as a "Y" site.
Figures 6, 7, 8:
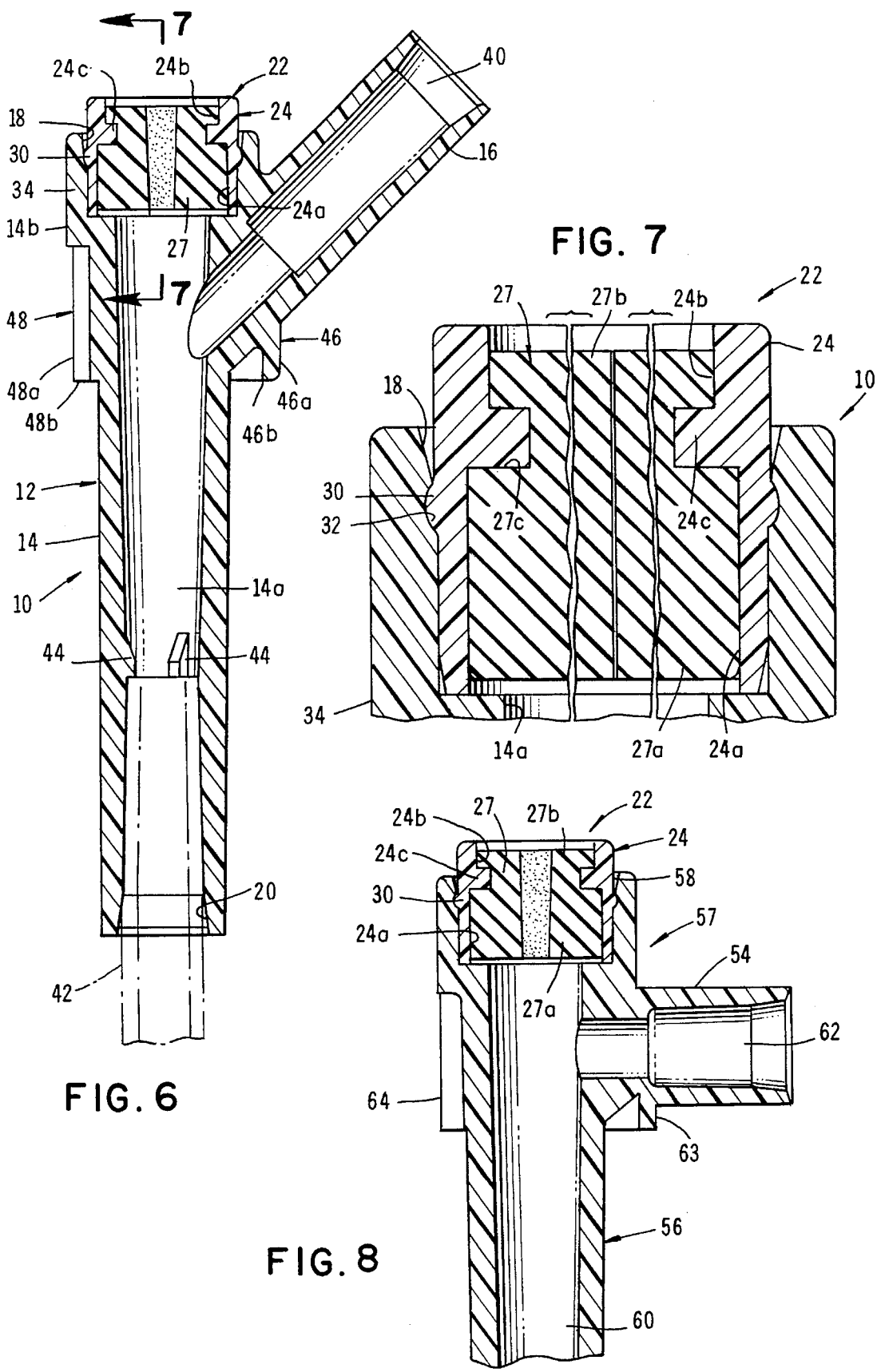
FIG. 6 is a cross-sectional view taken along lines 6—6 of FIG. 2.
FIG. 7 is a greatly enlarged, foreshortened, cross-sectional view taken along lines 7—7 of FIG. 6.
FIG. 8 is a fragmentary, cross-sectional view of an alternate form of the injection site of the infusion apparatus of the invention shown here as a "T" connector.

Referring to the drawings and particularly to FIGS. 1 and 7, one embodiment of the injection site of the infusion apparatus of the present invention is there shown and generally designated by the numeral 10. The injection site of this form of the invention comprises a low dead space Y site 12 unit which includes a tubular body portion 14 having a central passageway 14a and an arm portion 16 which extends laterally therefrom. The Y site also includes first and second end portions defining first and second ports 18 and 20 respectively, the first port 18 being defined by enlarged diameter portion 14a and being closed by a uniquely constructed closure means shown here as a closure assembly 22 (FIG. 1). Closure assembly 22 comprises a septum holding means, shown here as a generally cylindrically shaped ring-like member 24, and a split septum 27.

As best seen by referring to FIGS. 6 and 7, member 24 includes an inner wall which defines a septum chamber having an enlarged diameter first or lower subchamber 24a and a reduced diameter second or upper subchamber 24b. Subchambers 24a and 24b are divided by an inwardly extending annular segment 24c which comprises a part of the septum retaining means of the invention, the character of which will presently be described. The outer surface of member 24 is provided with a circumferentially extending protuberance 30 which comprises a part of the locking means of the invention for locking member 24 in position within port 18. Protuberance 30 is closely received within a groove 32 formed in the interior surface of wall 34 which defines first port 18 (FIG. 7).

Septum 27, which is constructed from a yieldably deformable elastomeric material, includes an enlarged diameter first or lower portion 27a which is closely received within subchamber 24a of member 24 and a reduced diameter upper or second portion 24b which is closely received within subchamber 24b of member 24. As indicated in FIG. 7, septum 27 is provided with a groove 27c which closely receives annular wall 24c so that the septum is securely retained in position within member 24. For reasons presently to be discussed, ring-like member 24 is preferably constructed from a plastic material that has enough resiliency to allow slight deformation of the skirt portion of the member.

In assembling the injection site shown in FIGS. 1 through 7, split septum 27 is mated with ring member 24 by inserting the elastomeric septum into subchamber 24a and then pushing it past segment 24c into the secured position shown in FIGS. 6 and 7. In this position it is to be noted that clearances provided between the septum and the ring-like member prevent the imposition of either radial or axial forces on the septum by the ring-like member.

After the septum is mated with member 24, the assemblage thus formed is mated with body portion 14 by inserting the assemblage into port 18 and exerting a force thereon which is sufficient to cause protuberance 30 to snap into groove 32. With the closure means thus mated with body portion 14 fluid can be introduced into passageway 14a by means of a cannula adapted to penetrate septum 27 or alternatively via third port 40 which is defined by the outer terminal portion of arm 16.

Fluid flowing through passageway 14a can be conducted to a patient via a conduit 42 which is telescopically receivable within second port 20 of the Y site in the manner shown in FIG. 6. To permit insertion of conduit 42 to the proper depth circumferentially spaced stop ribs 44 are formed on the inner wall of passageway 14b (see FIGS. 5 and 6).

An important feature of the Y site of the form of the invention shown in FIGS. 1 through 7, is the locking members or protuberances 46 and 48 which function to lockably engage locking means provided on one or more forms of the connector units of the invention, the character of which will presently be described. The configuration of protuberance 46 is best seen by referring to FIGS. 1 and 6 where it is to be noted that protuberance 46 includes a downwardly extending portion 46a which is connected to arm 16 and terminates in an edge 46b which is engagable by the locking means of the medical connectors of the invention. Protuberance 48 also includes a downwardly extending portion 48a which is connected to enlarged diameter portion 14a (FIG. 6) and which terminates in an edge 48b which is also engagable by the locking means of the medical connectors of the invention.

Turning now to FIG. 8, an alternate form of injection site of the invention is there shown. This injection site is similar in many respects to that shown in FIGS. 1 through 7 and like numerals are used to identify like components. The principal difference between the injection site of FIG. 8 and that previously discussed is that the side arm 54 extends from the tubular body portion 56 of the injection site at a right angle rather than at an acute angle. Like the Y site, this T site 57 has first, second and third ports 58, 60 and 62, with port 58 being closed by a closure assembly 22 identical to that previously described herein. T site 57 also includes locking protuberances 63 and 64 which are similar to protuberances 46 and 48 and which serve the same purpose.

Turning now to FIG. 8A, yet another alternate form of the invention is there shown. This device includes a central port which can function either as an infusion site or as a sampling port. The device is similar in some respects to the injection site shown in FIG. 8 and like numerals are used to identify like components. The principal difference between the device shown in FIG. 8A and that shown in FIG. 8 is that the device includes an elongated, generally tubular body portion 65 which is provided with at least one a centrally disposed site or sampling port. Like the "T" site, this in-line device 65 has first, second and third ports 58a, 60a, and 62a with port 58a being closed by a closure assembly 22 which is identical to that previously described herein. As best seen in FIG. 8C, wall 58b, which defines port 58a, is provided with generally "L" shaped bayonet type grooves L which receive protuberances "P" formed on wings "W" provided on the mating medical connector "M". (See also FIGS. 8B and 8D). Medical connector "M" includes a body portion "M–1" and a blunt cannula portion "C" which is of sufficient length to extend through split septum 27 and into fluid passageway "FP" which interconnects ports 60 and 62a (see FIG. 8B). Body portion "M–1" is provided with luer type threads "T" proximate its upper end for use in interconnecting the device with an appropriate conduit. As indicated in FIGS. 8E and 8F, each connector "M" is interconnected with device 65 by urging cannula "C" into split septum 27 so that protuberances "P" align with the legs "L–1" of the L shaped groves. After the cannula penetrates the septum, the connector is rotated in the manner shown in FIGS. 8E and 8F to urge protuberances "P" into portion "L–2" of the L shaped grooves. Once connected fluids flowing through passageway "FP" can be sampled, or alternatively, fluids can be added to passageway "FP".

Referring particularly to FIG. 8D, it is to be noted that two in-line sites can be provided in a spaced-apart construction so that passageway "FP" can be accessed at two locations for either sampling or infusion of fluids.

Referring next to FIGS. 9, 10 and 11, still another form of injection site 65 of the present invention is there illustrated. The tubular body portion 66 of this injection site is similar to body portion 14 and includes first and second end portions defining ports 68 and 70 which are interconnected by a central passageway 72. Also communicating with passageway 72 is a third port 73 provided in an angularly extending arm 75. Port 68 is closed by a closure means or closure assembly 74 which is of a slightly different construction than that of closure assembly 22. More particularly, closure assembly 74 comprises a differently configured, generally ring-shaped member, or septum holding means 76 within which is mounted a specially configured split septum 78.

As best seen in FIG. 10, ring-shaped member 76 has an outer wall 76a and an inner wall 76b which includes a first upper portion that defines a chamber 77 and a second, or lower, portion that cooperates with outer wall 76a to define an outwardly sloping, resiliently deformable skirt portion 79. Skirt portion 79 is closely received over a nipple-like tapered protuberance 80 formed on the tubular member 66 proximate end 72a of passageway 72. Tapered protuberance 80 cooperates with the inner surface of an enlarged diameter portion 66a of tubular body 66 to define a circumferentially extending groove 66b which closely receives skirt portion 79 of ring 76. To lockably interconnect ring 76 with protuberance 80, locking means are provided which here include a circumferentially extending, rounded bead-like protuberance 82 formed on nipple 80 (FIG. 11). In the manner shown in FIG. 10, bead-like protuberance 82 is received within a groove 84 provided on the inner surface of skirt portion 79 of ring 76.

To retain septum 78 within ring 76, retaining means are provided. The retaining means here comprise a generally annular shaped segment 85 which is integrally formed with and extends inwardly from the inner wall of ring-shaped member 76. To lockably receive segment 85, septum 78 is provided with a circumferentially extending groove 78a. With this construction, as septum 78 is inserted into ring member 76, segment 84 will snap into groove 78a thereby securely interlocking the parts together.

After septum 78 is mated with ring 76, the assemblage thus formed is mated with tabular body 66 in the manner shown in FIG. 11. More particularly, as skirt portion 79 enters groove 66b, it will ride over bead-like protuberance 82 and will snap into the locked position shown in FIG. 10. In this locked position, the lower extremity 78b of septum 78 will extend partially into central passageway 72.

Turning next to FIGS. 12 and 13, yet another form of injection site is there shown and generally designated by the numeral 90. Y site 90 also includes first, second and third ports 91, 92, and 93 and a closure means for closing port 91. The closure means here comprises a ring-like member 94 within which is carried a split septum 95. As best seen in FIG. 13, member 94 is lockably received within port 91 and is held in position therein by locking means which include a circumferential bead 96 that is received within a groove 97 that is provided in the enlarged diameter upper portion 98a of tubular body 98. Septum 95 is of somewhat similar construction to septum 78 and, like septum 78, includes a groove 95a within which is received an annular segment 94a formed on the inner surface of ring member 94. However, unlike septum 78, septum 95 is provided with a downwardly extending skirt-like portion 95b which extends into the central passageway of tubular body portion 98 a substantial distance.

Turning now to FIGS. 14 through 26, one form of medical connector of the apparatus of the invention is there shown and generally identified by the numeral 100. The connector of this form of the invention is adapted for use with a variety of different types of entry port structures, including Y sites and T sites of the character shown in FIGS. 1 through 8. Connector 100 comprises a base or end wall 102 and a blunt cannula 104 connected thereto and extending outwardly therefrom. Integrally formed with base 102 are locking means for locking engagement with the locking members of the particular entry port structure with which it is to be mated such as, for example, protuberances 46 and 48. The locking means here include a pair of resiliently deformable side members 106 which are generally "C" shaped in cross section (FIG. 17). Side members 106 extend along either side of cannula 104 and, in their normal state, are disposed in a generally parallel relationship with to the longitudinal axis of the cannula.

The cannula shown in FIGS. 14 through 26 comprises a plastic cannula having a tapered wall, one end of which interconnects with base 102 in the manner best seen in FIG. 16. The opposite end of the cannula terminates in a septum penetrating extremity 104a which includes a tip portion that is configured to readily penetrate a split or slitted septum of the character shown in the drawings. Cannula 104 may be integrally formed with base 102 or, in some instances, may comprise a separate element which is either fixedly or removably interconnected with base 102.

Extending rearwardly of base 102 is a connecting portion 108 having a fluid passageway 110 which communicates with a fluid passageway 112 that extends axially of cannula 104. Portion 108 can be suitably interconnected with a source of liquid such as parenteral fluid by means of a luer connector, a length of plastic tubing or in other ways well known to those skilled in the art.

Also forming a part of the locking means of the present embodiment of the invention are oppositely disposed barb-like locking segments 114 which are preferably integrally formed with the "C" shaped side members 106 of the connector. As indicated in FIGS. 21 through 23, inboard extremities 114a of the locking segments are adapted to lockably engage locking protuberances such as locking protuberances 46 and 48 provided on the Y site 12. Forwardly of extremities 114a are inwardly sweeping curved surfaces 114b (FIG. 16), which guide entrance of protuberances 46 and 48 between the locking segments as the connector is mated with the Y site.

Side members 106 are constructed of a relatively thin plastic material which is yieldably deformable so that as the protuberance 46 and 48 pass between curved surfaces 114b, the side members will spread apart a sufficient distance to permit the protuberances to pass by and then to snap into a locked position about the protuberances in the manner shown in FIG. 25.

The apparatus of the present form of the invention also includes release means for moving the locking means from a locked position to an unlocked position. The release means here functions to spread apart barb-like segments 114 a sufficient distance to permit the passage therebetween of protuberances 46 and 48 of the Y site as the connector is separated from the Y site. More specifically, the release means here comprises a pair of spaced-apart, wing-like gripping members 118 which, as best seen in FIGS. 14, 15, and 17, extend outwardly from side members 106. Gripping members 118 are provided with rounded, non-snag corners, and with gripping striations 120 which provide a textured surface to facilitate gripping the members in a manner to positively urge them toward one another. Due to the resilient character of the plastic, as the gripping members are urged toward one another, segments 114 of side members 106 will move from their first, at-rest or locked position (FIG. 23) to their second, or open, unlocked position (FIG. 25) wherein the space between the elements is sufficient to permit passage of protuberances 46 and 48 of the Y site unit. To facilitate the release step, side walls 106 are provided with circumferentially extending relief slits 107. With the gripping members urged toward one another, the protuberances on the Y site will clear the locking edges of the protuberances permitting smooth and easy disconnection of the connector from the Y site unit. As in the earlier described embodiments of the invention, the configuration of the wing-like gripping members is such that they also provide a flat patient-engaging surface or base to permit the device to be positively and securely tapered to the patient in a stable mannet.

In the form of the invention shown in FIGS. 14 through 26 of the drawings, second locking means are also provided for releasably locking the connector to the Y site. This second locking means is here provided in the form of a pen snap type lock which comprises circumferentially extending beads 124 located on the inner surfaces of sides 106. Beads 124 are uniquely formed and, as shown in FIG. 26, are of a greater thickness proximate one end thereof. As the head portion of the Y site enters the connector it will frictionally engage bead 124. Then, upon the continued exertion of an inward force on the Y site, the head portion 14a thereof (see FIGS. 22 and 23) will slip by bead 124 of the Y site and move into locking engagement with the lower peripheral edge 15 of portion 14a.

Connector 12 is preferably constructed from a durable, springy clear plastic material that can be injection molded and one that is fully compatible with commonly used drugs and parenteral fluids.

Turning now to FIGS. 27 through 33, the use of the previously described medical connector 100 with a low dead space heparin lock 129 of the present invention is there illustrated. As best seen in FIG. 27, one form of the low dead space heparin lock of the invention comprises a tubular body portion 130 having an enlarged diameter head portion 132. The heparin lock also includes first and second ports 134 and 136, the first port 134 being closed by a uniquely constructed closure means of the general character previously described. An important feature of the heparin lock of this form of the invention, is the locking protuberances 138 and 140 which function to lockably engage the barb-like segments 114 provided on the side members of the connector unit. The configuration of protuberance 138 is best seen by referring to FIG. 28 where it is to be noted that the protuberance includes a plate-like portion 138a which is connected to a body portion 132a which terminates in a locking edge 138b. Protuberance 140 also includes a plate-like body portion 140a which terminates in a locking edge 140b. Locking edges 138b and 140b are engagable by segments 114 in the manner previously described.

The heparin lock of the invention also includes an enlarged diameter portion 142 disposed at the opposite end of the tubular body portion 130 from head 132. As best seen in FIG. 29, portion 142 surrounds the inwardly tapering end portion 130d of body 130 and includes a plurality of circumferentially spaced gripping beads 142a (FIG. 27). Lockably receivable within portion 142 is a connector member of standard construction (not shown).

As best seen in FIG. 29, port 134 is closed by a closure assembly 22 which is identical to that previously described in connection with the embodiment of the invention shown in FIGS. 1 through 7. More particularly, closure assembly 22 comprises a septum holding means, shown here as a generally cylindrically shaped ring-like member 24, and a split septum 27. The nature of these components and their method of assembly with the inlet port of the site is as previously described and like numerals are used to identify like components.

Figure 34:
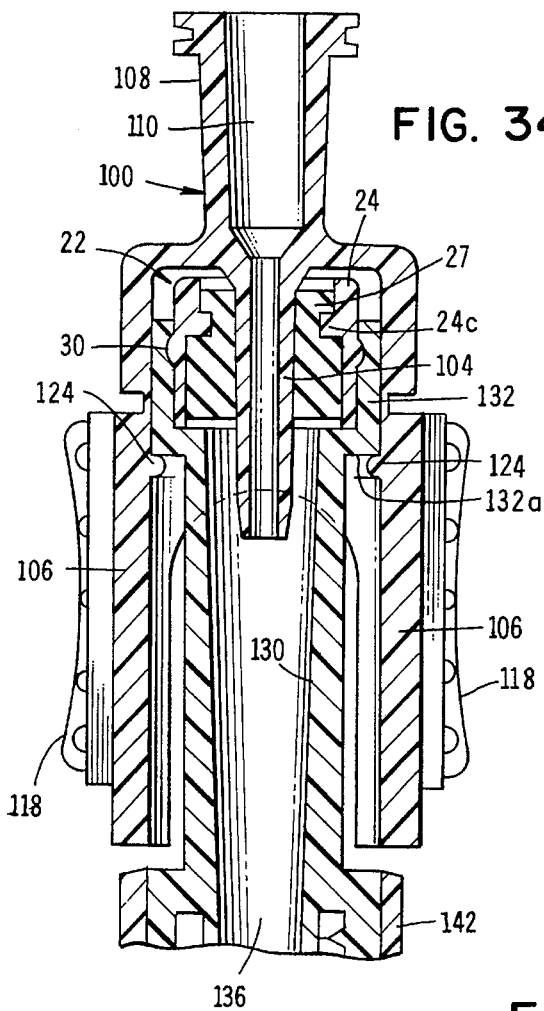
FIG. 34 is a cross-sectional view taken along lines 34—34 of FIG. 33.

In using the apparatus of the invention, the medical connector 100 is interconnected with a suitable source of liquid to be infused in the patient such as a parenteral liquid contained within a suitable source such as a bottle or elevated flexible bag. The medical connector can then be coupled with a selected injection site, such as Y site 14 (FIG. 1), T site 54 (FIG. 8), Y site 65 (FIG. 9), Y site 90 (FIG. 12), or heparin lock 129 (FIG. 27) in the following manner: First the septum carrying end on the injection site is inserted into the open mouth of the connector 100 (FIG. 21) and urged inwardly between sides 106 with sufficient force to cause the cannula to penetrate the septum. As the injection site is introduced into the medical connector 100, the locking protuberances of the injection site will ride along curved surfaces 114b or segments 114 (FIGS. 21, 22 and 31) urging sides 106 to separate. Because of the resilient nature of sides 106 they will be permitted to resiliently deform outwardly a sufficient distance to allow the protuberances of the injection site to slide past segments 114 and to snap into the locking position shown in FIGS. 23, 32, and 33. As the protuberances snap into a locking position, both an audible sound will result and a tactile sensation will be experienced by the technician interconnecting the components. A further tactile signal is given to the technician by the previously described, second pen snap locking means of the invention which comprise protuberances 124. (See also FIGS. 23 and 34). In the manner shown in FIG. 34, beads or protuberances 124 snap under the peripheral edge 132a of head portion 132 to provide the tactile signal.

With the medical connector 100 and the selected injection site interconnected in the manner thus described, the injection site will be securely and stably maintained in position within the connector without any appreciable wobbling or without any pistoning of the cannula within the septum. When it is desired to disconnect the components, an inward force exerted on wings or gripping members 118 will cause elements 114 to separate a sufficient distance to permit passage thereby of the locking protuberances of the injection site so that the injection site can be smoothly and easily disconnected from the connector 100. (See FIGS. 25 and 26).

Referring now to FIGS. 36 through 44 an alternate form of medical connector of the apparatus of the present invention is there illustrated and generally identified by the numeral 150. This medical connector, like the medical connector 100 previously described, is usable with a number of different types of injection sites including the heparin lock type injection site illustrated in FIG. 36. Connector 150 comprises a generally cylindrically shaped base portion 152 and a blunt cannula 154 connected thereto and extending outwardly therefrom. Integrally formed with base 152 are locking means for locking engagement with an entry port structure such as the heparin lock shown in FIG. 36. The locking means here comprise a pair of resiliently deformable side members 156 which are generally "L" shaped and which are interconnected with cylindrical base 152 in the manner shown in FIG. 36. Side members 156 extend to either side of cannula 154 and, in their normal state, are generally parallel to the longitudinal axis of the cannula.

Figure 36:
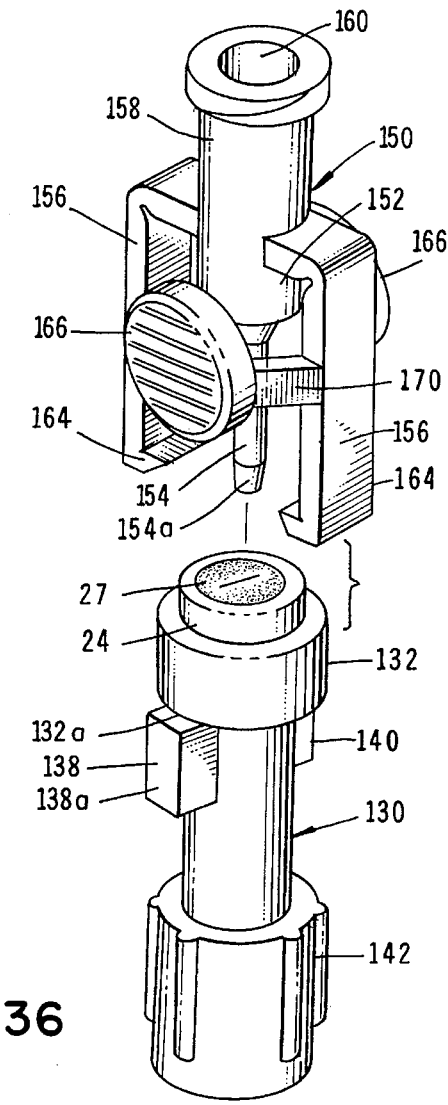
FIG. 36 is a generally perspective view of an alternate form of the infusion apparatus of the present invention.
Figure 35:
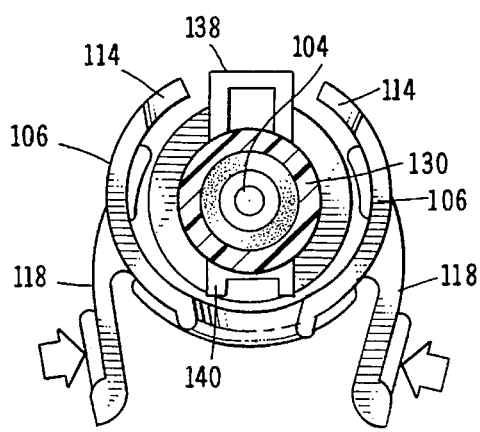
FIG. 35 is a bottom view, partly in cross-section showing a component separating force being exerted upon the wings of the medical connector.
Figures 38, 39, 40:
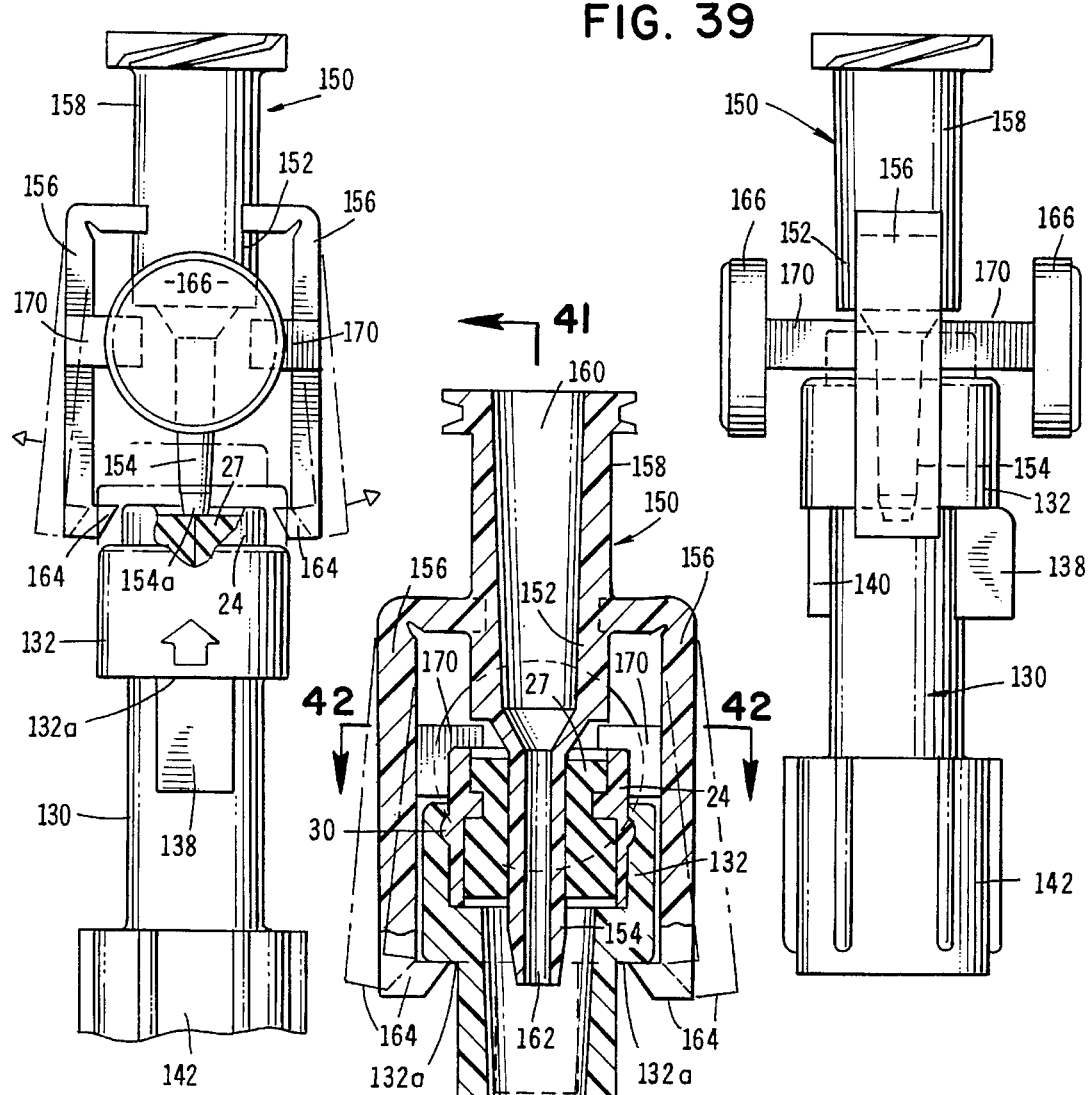
FIG. 38 is an enlarged, front-elevational view of the medical connector of FIG. 36 in an initial mating position with the injection site of FIG. 36.
FIG. 39 is a side elevation view similar to FIG. 38 but showing the component parts in a mated configuration.
FIG. 40 is an enlarged, cross-sectional view of the assemblage of FIG. 39.
Figure 41:
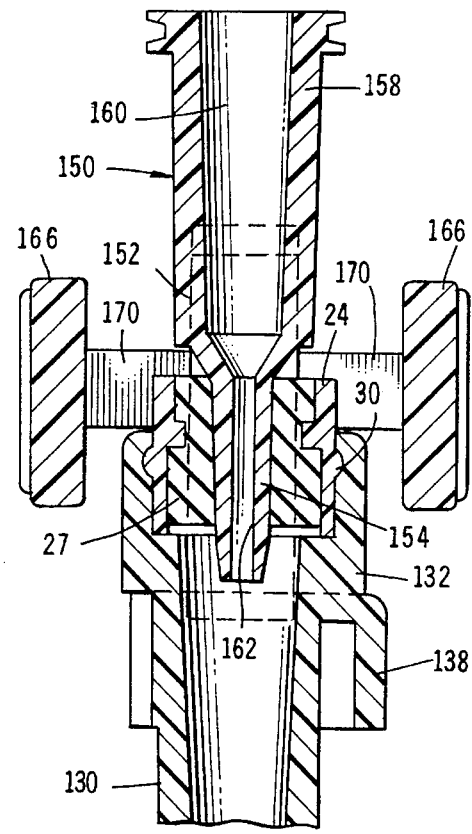
FIG. 41 is a cross-sectional view taken along lines 41-14 of FIG. 40.
Figure 43:
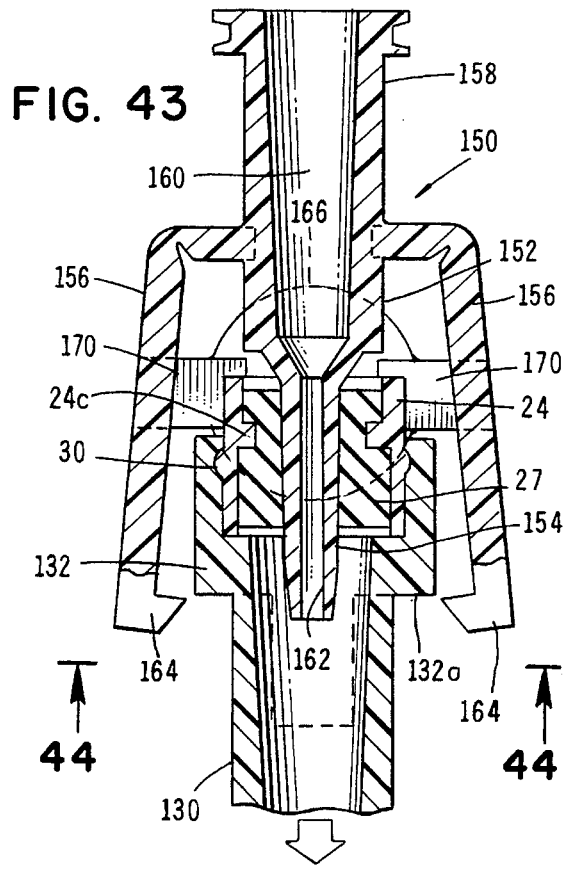
FIG. 43 is a side elevational view similar to FIG. 41, but showing the position of the parts upon applying a separating force on the finger pads of the medical connector.
Figure 42:
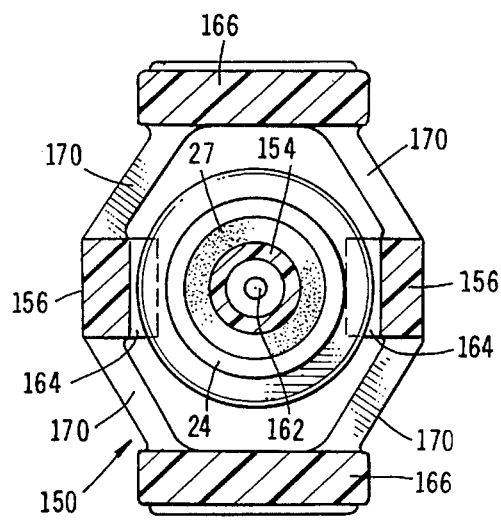
FIG. 42 is a cross-sectional view taken along lines 42—42 of FIG. 40.
Figure 44:
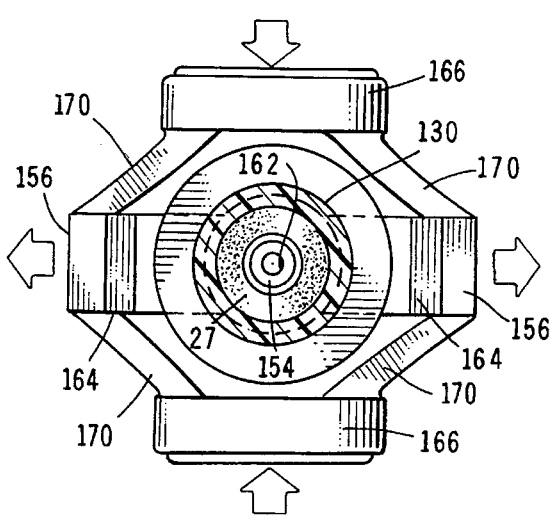
FIG. 44 is a view taken along lines 44—44 of FIG. 43.
Figure 48:
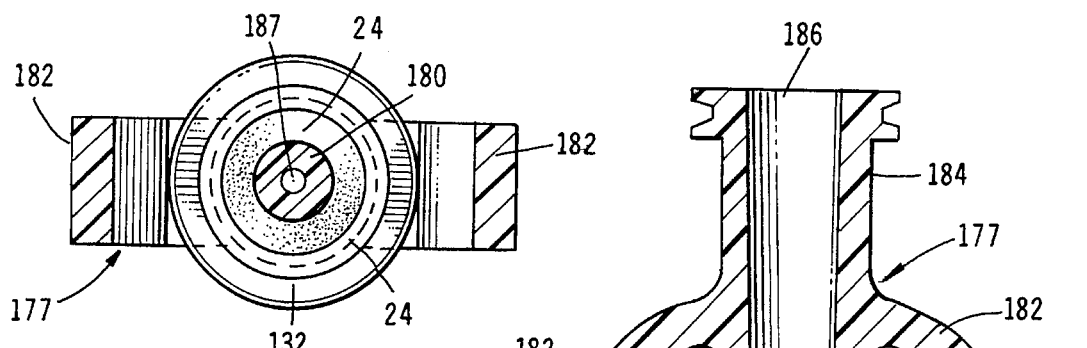
FIG. 48 is a cross-sectional view taken along lines 48—48 of FIG. 47.

The cannula shown in FIGS. 36, 38, and 40 comprises a plastic cannula having a tapered wall, one end of which interconnects with base 152 and the opposite end of which terminates in a septum penetrating extremity 154a. As before, tip portion 154a is adapted to readily penetrate a split septum of the character shown in the drawings.

Extending rearwardly of base 152 is a connecting portion 158 which has a fluid passageway 160 which communicates with a fluid passageway 162 which extends through cannula 154 (FIG. 40). As before, portion 158 can be suitably interconnected with a source of liquid such as a parenteral fluid by means of a luer connector or a similar connector known to those skilled in the art.

Also forming a part of the locking means of this latest form of the invention are oppositely disposed locking segments 164 which are integrally formed with side members 156. As best seen by referring to FIG. 40, segments 164 are adapted to lockably engage the lower peripheral surface 132a of head portion 132 of the heparin lock.

Figure 37:
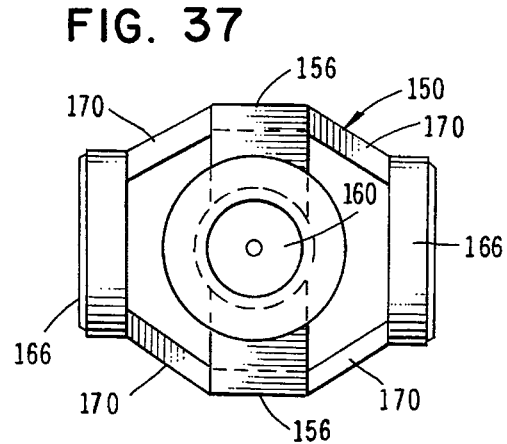
FIG. 37 is an enlarged top view of the connector shown in FIG. 36.

The apparatus of this latest form of the invention also includes release means for removing the locking means from the locked position shown in the solid lines of FIG. 40 to a unlocked position shown by the phantom lines of FIG. 40. More particularly, the release means here functions to spread apart locking segments 164 a sufficient distance to permit the passage therebetween of head portion 132 of the injection site. As best seen by referring to FIGS. 36 and 39, the release means here comprise a pair of pressure pads which are disposed on opposite sides of cannula 154 and which are movable toward and away from the cannula by inward forces directed on the pads in the manner illustrated in FIG. 44. To interconnect pressure pads 166 with side members 156, two pair of strut means are provided. Each pair of strut means comprises first and second strut members 170. Each member having first and second ends. The first end of each member is connected with one of the pads 166 while the other end of the strut member is connected to selected one of the side members 156 (FIGS. 37 and 39). With this construction, when struts 170 are in their normal static position shown in FIG. 42, segments 164 will be retained beneath peripheral surface 132a of head portion 132 in the manner shown in FIG. 42. An inward force directed on pads 162 in the direction of the arrows of FIG. 44 will cause side members 156 along with locking segments 164 to move outwardly in the direction shown in FIG. 43 and 44 permitting the head portion 132 of the injection site to pass between the locking segments 164.

Due to the resiliently deformable nature of side members 156, during assembly of the medical connector with the injection site, in the manner shown in FIG. 40, locking segments 64 will ride along the sides of upper portion 132 of the injection site as the septum is pierced by the cannula. When the cannula reaches the position as shown in FIG. 40 where it extends completely through the septum, the spring forces within side members 156 will cause the locking segments 164 to snap into a locking position shown by the solid lines in FIG. 40.

Referring now to FIGS. 45 through 50 still another form of medical connector of the apparatus of the present invention is there illustrated and generally identified by the numeral 177. This medical connector, like those previously described, is usable with a number of different types of injection sites including the heparin lock type injection site illustrated in FIG. 45. The connector can also be used with the Y-site shown in FIG. 6, with the T-site shown in FIG. 8 and with the sampling port shown in FIG. 8A. Connector 177 comprises a generally cylindrically shaped base portion 178 and a blunt cannula 180 connected thereto and extending outwardly therefrom. Integrally formed with base portion 178 are locking means for locking engagement with an entry port structure such as the heparin lock shown in FIG. 45. The locking means here comprise a pair of resiliently deformable curved side members 182 which are interconnected with cylindrical base 178 in the manner best seen in FIGS. 45 and 47. Side members 182 extend to either side of cannula 180 and, in their normal state, the lower portions thereof extend substantially parallel to the longitudinal axis of the cannula.

Figure 49:
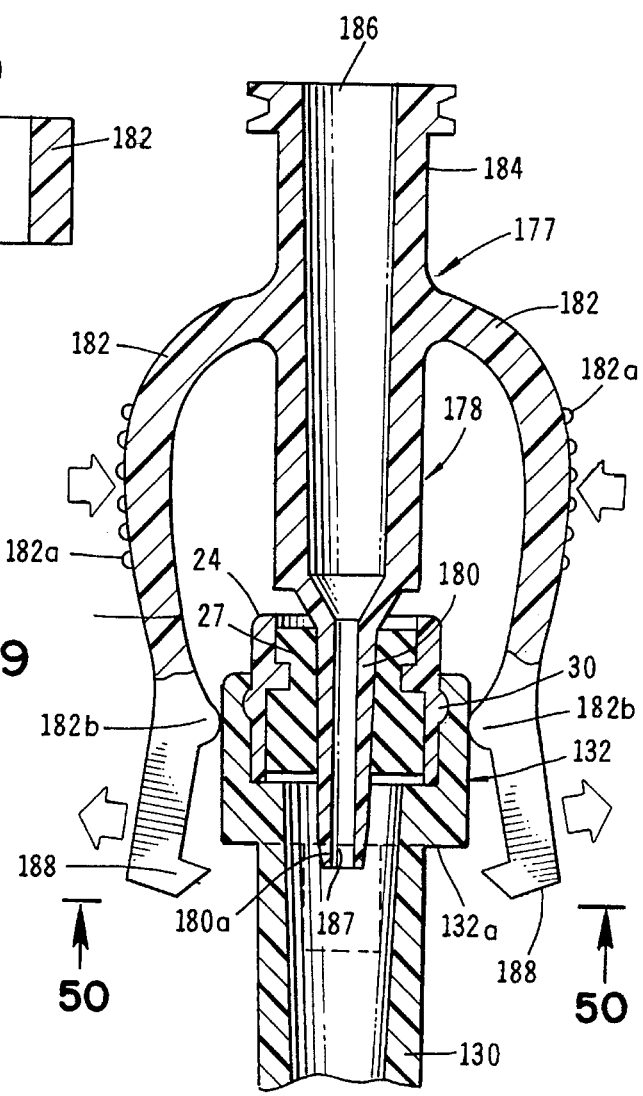
FIG. 49 is a front elevational view similar to FIG. 47, but showing the position of the parts after a separating force has been directed upon the medical connector.
Figure 50:
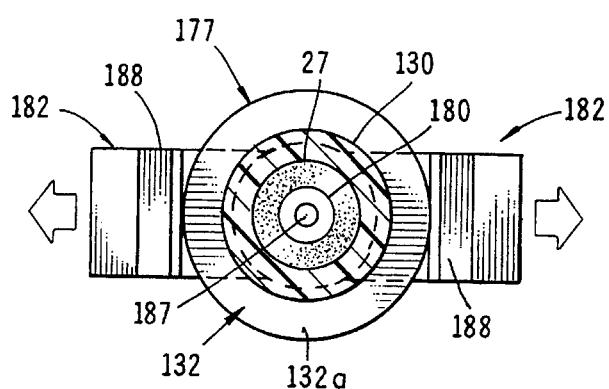
FIG. 50 is a view taken along lines 50—50 of FIG. 49.
Figure 51:
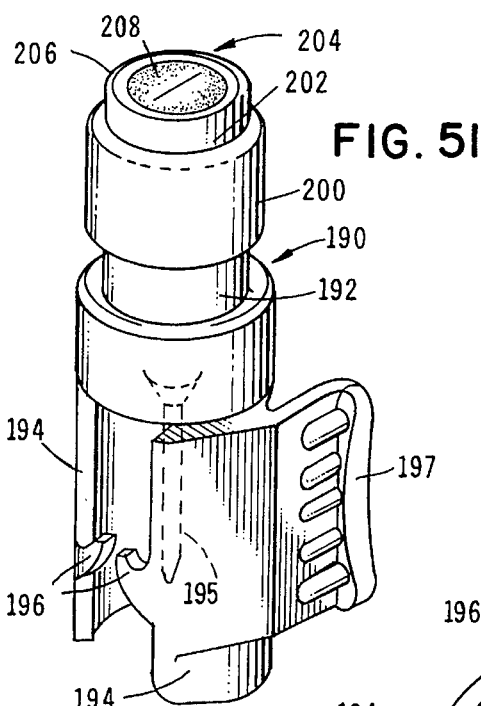
FIG. 51 is a generally perspective front view of still another form of medical connector of the infusion apparatus of the present invention.
Figure 52:
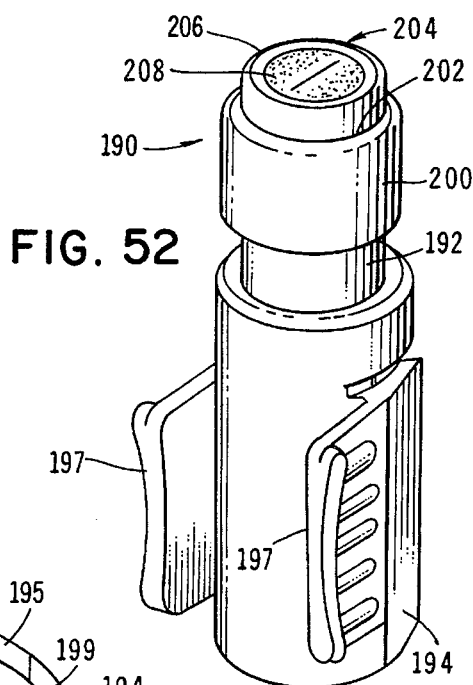
FIG. 52 is a generally perspective, rear view of the medical connector of FIG. 51.

The cannula shown in FIGS. 45, 47, and 49 comprises a plastic cannula having a tapered wall, one end of which interconnects with base 178 and the opposite end of which terminates in a septum penetrating extremity 180*a*. As before, tip portion 154*a* is adapted to readily penetrate a split septum of the character shown in the drawings.

Extending rearwardly of base 178 is a connecting portion 184 which has a fluid passageway 186 which communicates with a fluid passageway 187 which extends through cannula 180 (FIG. 47). As before, portion 186 can be suitably interconnected with a source of liquid such as a parenteral fluid by means of a luer connector or a similar connector known to those skilled in the art.

Also forming a part of the locking means of this latest form of the invention are oppositely disposed hook-like locking segments 188 which are integrally formed with side members 182. As best seen by referring to FIG. 47, segments 188 are adapted to lockably engage the lower peripheral surface 132*a* of head portion 132 of the heparin lock.

The apparatus of this latest form of the invention also includes release means for removing the locking means from the locked position shown in the solid lines of FIG. 47 to a unlocked position shown by the phantom lines of FIG. 47. More particularly, the release means here functions to spread apart locking segments 188 a sufficient distance to permit the passage therebetween of head portion 132 of the injection site. As best seen by referring to FIGS. 47 and 49, the release means here comprises curved pressure pads which are exerting areas 182*a* formed on sides 182. Also comprising a part of the release means are fulcrum-like protuberances 182*b* formed on sides proximate locking segments 188. With this construction, segments 188 are movable into the release position shown in FIG. 49 by the exertion of inward forces on areas 182*a* in the manner illustrated by the arrows in FIG. 49. More particularly, as forces are exerted on areas 182*a*, protuberances 182*b* will engage portion 132 of the injection site causing segments to swing outwardly about protuberances 182*b* in the manner shown in FIG. 49. As seen in FIG. 47, when sides 182 are in their normal static position there shown segments 188 will be retained beneath peripheral surface 132*a* of head portion 132 in the manner shown by the solid lines in FIG. 47. Segments 188 will remain in this position until an inward force is directed on areas 182*a* causing locking segments 188 to move outwardly so as to permit head portion 132 of the injection site to pass between the locking segments.

Due to the resiliently deformable nature of side members 182, during assembly of the medical connector with the injection site, the locking segments will ride along the sides of upper portion 132 of the injection site as the septum is pierced by the cannula. When the cannula reaches the position as shown in FIG. 47 where it extends completely through the septum, the spring forces within side members 182 will cause the locking segments 188 to snap into a locking position shown by the solid lines in FIG. 47.

Figure 54:
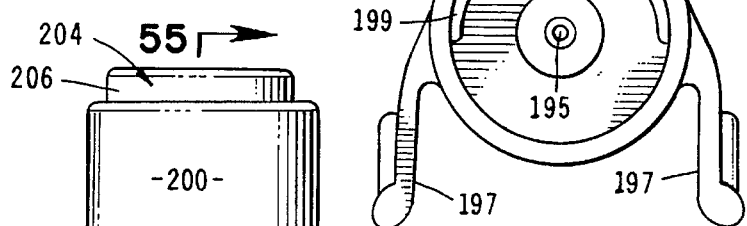
FIG. 54 is a view taken along lines 54—54 of FIG. 53.
Figure 53:
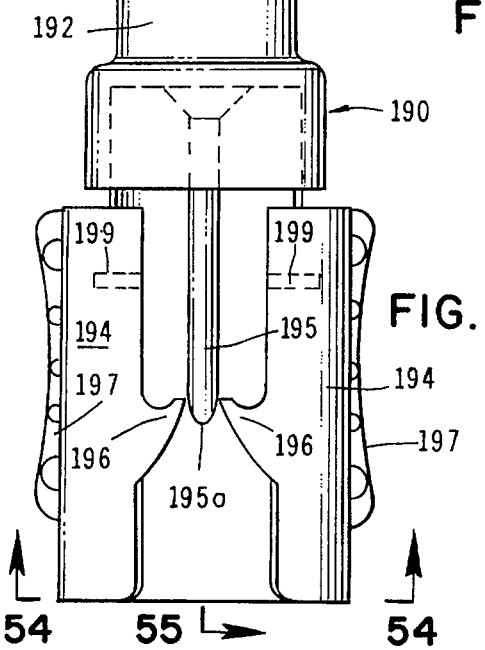
FIG. 53 is an enlarged front view of the medical connector shown in FIG. 51.
Figure 55:
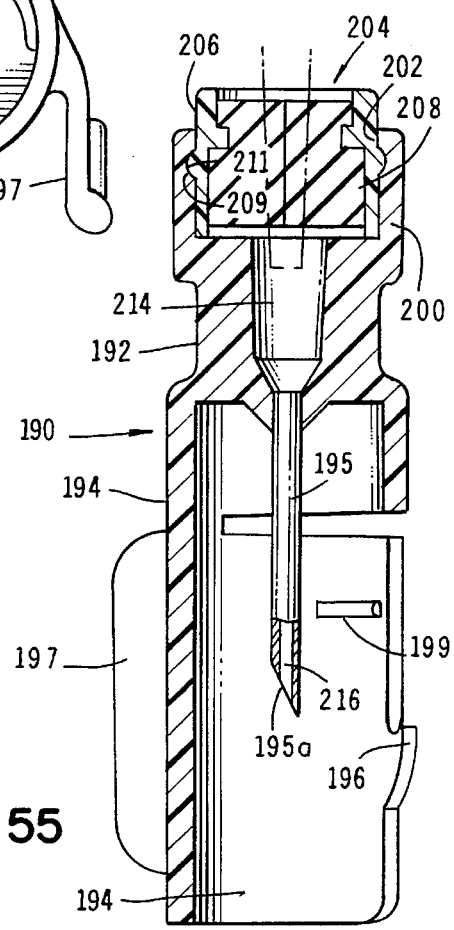
FIG. 55 is a cross-sectional view taken along lines 55—55 of FIG. 53.

Referring to FIGS. 51 through 55, another form of medical connector of the apparatus of the invention is there shown and generally identified by the numeral 190. The connector of this form of the invention is adapted for use with entry port structures, including Y sites, T sites and heparin locks of the character having conventional needle pierceable septums. As best seen in FIG. 55, connector 190 comprises a generally cylindrical base 192 and a metal cannula or hollow needle 195 connected thereto and extending outwardly therefrom. Integrally formed with base 192 are locking means for locking engagement with the locking members of the particular entry port structure with which it is to be mated. The locking means are identical to those described in connection with FIGS. 14 through 26 and include a pair of resiliently deformable side members 194 which are generally "C" shaped in cross section (FIG. 54). Side members 194 extend along either side of needle 194 and, in their normal state, are disposed in a generally parallel relationship with to the longitudinal axis of the needle.

The needle shown in FIGS. 51 through 55 comprises a hollow metal needle which terminates in a tapered septum penetrating extremity 195*a* which includes a tip portion that is configured to readily penetrate a conventional elastomertic septum. Needle 195 may be integrally formed with base 192 or, in some instances, may comprise a separate element which is either fixedly or removably interconnected with base 192.

Extending rearwardly of base 192 is a highly novel adapter means for adapting the connector for use with a device having a blunt cannula. The character of this adapter means and the method for using it will presently be discussed.

Also forming a part of the locking means of the medical connector of this embodiment of the invention are oppositely disposed barb-like locking segments 196 which are preferably integrally formed with the "C" shaped side members 194 of the connector. Locking segments 196 are of identical construction to previously described segments 114 and are adapted to lockably engage locking protuberances such as locking protuberances 46 and 48 provided on the Y site 12. A second pen snap locking means in the form of protuberances 199 are also provided in this form of the invention and operates in the manner earlier described.

Side members 194 are constructed of a relatively thin plastic material which is yieldably deformable so as to permit mating of the connector with the selected injection site in the same manner as previously described herein. Side members 194 also include release means in the form of wing-like gripping members 197 for moving the locking means from a locked position to an unlocked position in the manner previously described. Due to the resilient character of the plastic, as the gripping members are urged toward one another, segments 196 of side. members 194 will move from their first, at-rest or locked position (FIG. 53) to a second, or open, unlocked position wherein the space between the elements is sufficient to permit passage of the locking protuberances of the injection site unit.

In the form of the invention shown in FIGS. 51 through 55 of the drawings, the important adapter means comprises a cylindrical portion 200 which is integrally formed with base 192 and defines at its open end a port 202. Port 202 is closed by a closure means shown here as a closure assembly 204. Closure assembly 202 is identical to the previously described closure assembly 22 and comprises a septum holding means, shown here as a generally cylindrically shaped ring-like member 206, and a split septum 208. As before the outer surface of member 206 is provided with a circumferentially extending protuberance 209 which comprises a part of the locking means of the invention for locking member 206 in position within port 202 (FIG. 55). Protuberance 209 is closely received within a groove 211 formed in the interior surface of member 206.

Septum 208, which is constructed from a yieldably deformable elastomeric material, is locked into ring 206 in the same manner as septum 27 is locked into member 24 of the Y site of FIG. 1. After the septum is mated with member 206, the assemblage thus formed is mated with portion 200 by inserting the assemblage into port 202 and exerting a force thereon which is sufficient to cause protuberance 209 to snap into groove 211. With the closure means thus mated with portion 200, fluid can be introduced into a passageway 214 formed in base 192 (FIG. 55) by means of a cannula adapted to penetrate septum 208. Passageway 214 is in communication with the interior passageway 216 of needle 195 in the manner shown in FIG. 53.

Figure 2:
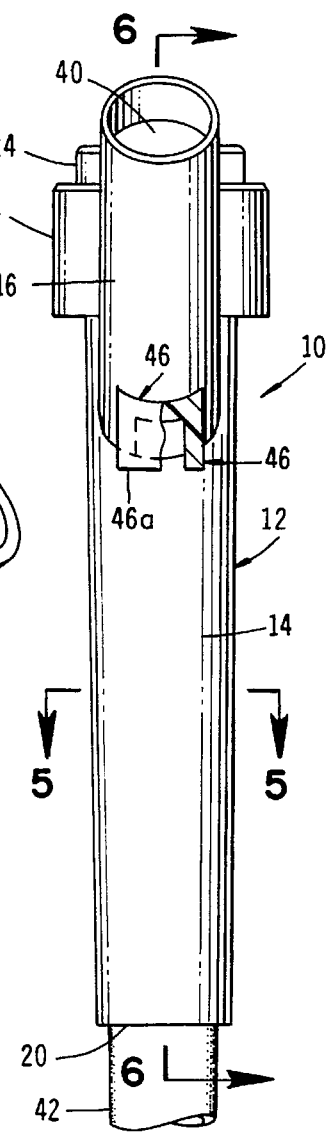
FIG. 2 is a front view of the "Y" site of FIG. 1.
Figure 3:
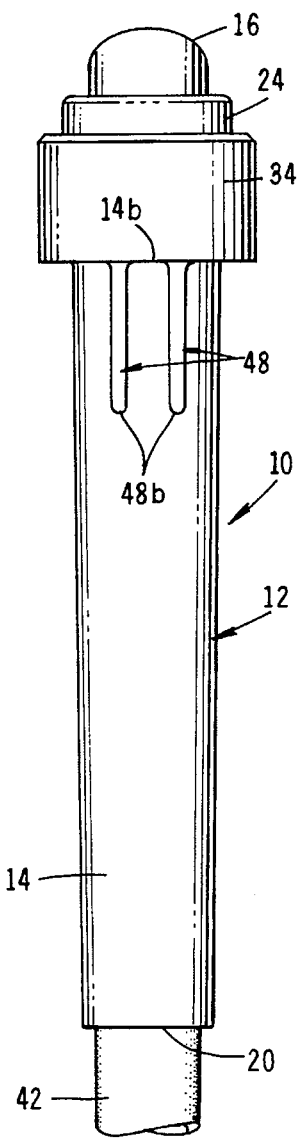
FIG. 3 is a rear view of the "Y" site of FIG. 1.
Figure 4:
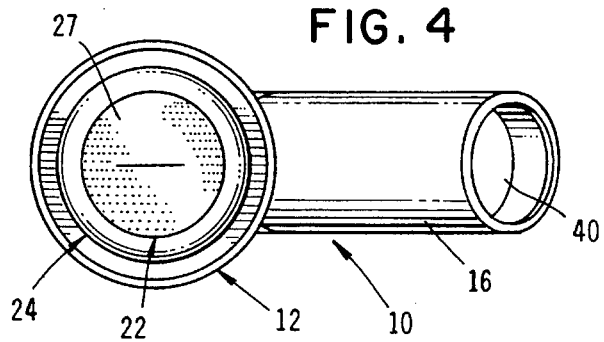
FIG. 4 is a top view of the "Y" site of FIG. 1.
Figure 5:
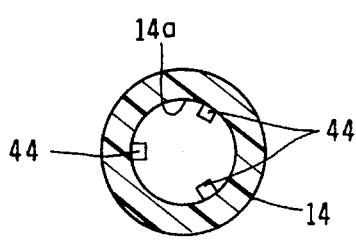
FIG. 5 is a cross-sectional view taken along lines 5—5 of FIG. 2.

After connector 190 is mated with a Y site, or similar injection site, such as shown in FIGS. 1 and 8, fluid flowing through passageway 214 can be conducted to a patient via needle 195 and a suitable conduit which is telescopically receivable within the second port of the Y site or T site in the manner shown in FIGS. 2, 3, and 6.

Figure 56:
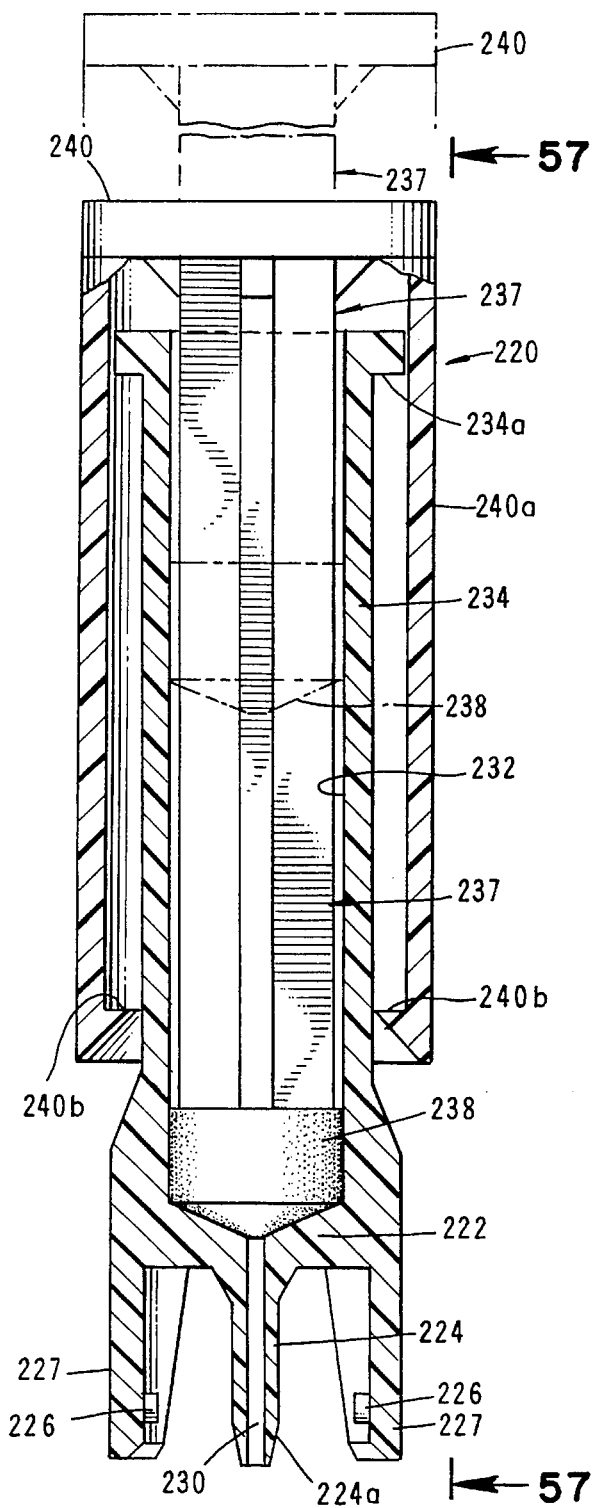
FIG. 56 is a cross-sectional view of a further alternate form of injection site of the invention.
Figure 57:
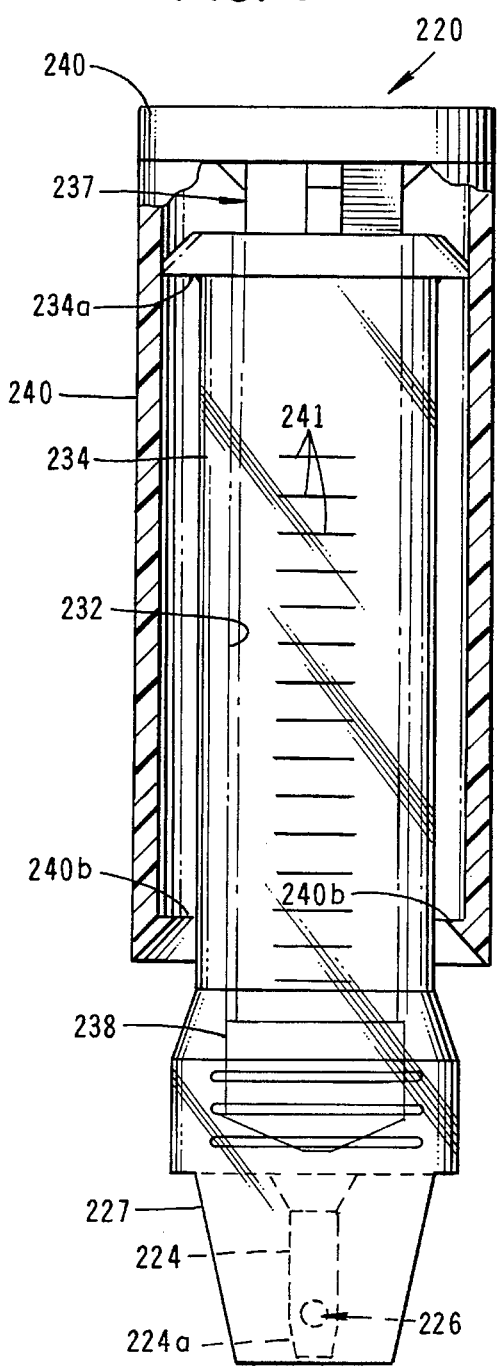
FIG. 57 is a view taken along lines 57—57 of FIG. 56.

Turning now to FIGS. 56 and 57, yet another form of medical connector of the apparatus of the invention is there shown and generally identified by the numeral 220. The connector of this form of the invention is adapted for use with devices of the character shown in FIGS. 8A through 8F, which devices were earlier described. Connector 220 comprises a base or end wall 222 and a blunt cannula 224 connected thereto and extending outwardly therefrom. Integrally formed with base 102 are locking means for locking engagement with the devices shown in FIGS. 8A through 8F, shown here as protuberances 226 which are formed on sidewall portions 227 and are adapted to be lockably received within the L shaped grooves of the devices of FIG. 8A through 8F.

Cannula 224 comprises a plastic cannula having a tapered wall, one end of which interconnects with end wall 222 in the manner best seen in FIG. 56. The opposite end of the cannula terminates in a septum penetrating extremity 224a which includes a tip portion that is configured to readily penetrate a split or slitted septum of the character shown in the drawings. Cannula 224 is provided with an internal passageway 230 which communicates with a chamber 232 formed by an upstanding cylindrical wall 234 which is integrally formed with base wall 222.

Receivable within chamber 232 is a plunger assembly 237 comprising an elastomeric plunger 238 which is reciprocally movable within chamber 232 in the manner shown by the phantom lines of FIG. 56 by a handle portion 240 which is connected to plunger 238. Handle portion 240 and plunger 238 comprise a part of the filling and dispensing means of the invention for urging fluid into the chamber from a fluid source as the plunger is moved upwardly within chamber 232 and for dispensing fluid from the chamber upon downward movement of the plunger. As indicated in FIG. 57, wall 234 is preferably transparent and is provided with indicia 241 which can be used to measure fluid level within chamber 232.

Integrally formed with handle portion 240 is a shield means, here shown as a downwardly depending, cylindrical skirt portion 240a which surrounds wall 234 and functions as a contamination shieled to prevent contamination in Chamber 232. A shoulder 240b is formed proximate the lower edge of skirt portion 240a and is adapted to engage an upper shoulder 234a formed on wall 234 to stop upward movement of handle portion 240 and plunger 238. With this construction, fluid can be drawn into chamber 232 via cannula 224 by upward movement of plunger 238 and can be expelled from cannula 224 by downward movement of the handle 240 and plunger 238.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An entry port structure usable with a cannula, comprising:
   (a) a tubular body having a centrally disposed fluid passageway and first and second ports in communication with said passageway; and
   (b) closure means for closing said first port of said tubular body, said closure means comprising:
      (i) septum holding means for holding a septum, including a generally ring shaped member telescopically received within said first port, said member having an inner wall defining a chamber and including septum retaining means for retaining a septum in said chamber said retaining means comprising a segment extending inwardly from said inner wall into said chamber; and
      (ii) a septum disposed within said chamber, said septum being penetrable by the cannula, and having a groove for receiving said segment of said ring shaped member.

2. An entry port structure as defined in claim 1 further including locking means for locking said closure means within said first port.

3. An entry port structure as defined in claim 1 in which said member of said septum holding means comprises a generally ring shaped member and in which said segment of said retaining means comprises a generally annular shaped segment, integrally formed with and extending radially inwardly from, said inner wall.

4. An entry port structure as defined in claim 3 in which said inner wall of said generally ring shaped member comprises first and second portions said first portion defining a first subchamber having a first diameter and said second portion defining a second subchamber having a second diameter.

5. An entry port structure as defined in claim 4 in which said septum includes a first enlarged diameter portion disposed within said first subchamber, a second reduced diameter portion disposed within said second subchamber, said groove being formed intermediate said first enlarged diameter portion and said second reduced diameter portion.

6. An entry port structure as defined in claim 4 which said septum is provided with a cannula receiving slit.

7. An entry port structure as defined in claim 4 which said tubular body is provided with a third port in communication with said central passageway.

8. An apparatus for infusing liquids from a liquid source into a patient comprising:
   (a) an entry port structure having a tubular body, said tubular body having a locking member and first and second ports, said first port being closed by closure means comprising:
      (i) a generally ring shaped member telescopically received within said first port said member having an inner wall defining chamber and including a septum retaining means for retaining a septum in said chamber, said retaining means comprising a radially inwardly extending segment extending from said wall into said chamber; and
      (ii) a septum mounted within said generally ring shaped member said septum having a groove for receiving said radially inwardly extending segment of said generally ring shaped member; and
   (b) a connector for releasable interconnection with said entry port structure, said connector comprising:

(i) a base;

(ii) a cannula connected to said base and extending therefrom; and (iii) locking means connected to said base and extending therefrom for locking engagement with said locking member of said entry port structure to lockably interconnect said connector with said entry port structure, said locking means being movable from a first locked position to a second unlocked position.

9. An apparatus as defined in claim 8 which said locking means comprises a pair of resiliently deformable spaced-apart, oppositely-disposed side members connected to said base, said cannula being disposed intermediate said side members.

10. An apparatus as defined in claim 9 which said cannula has a longitudinally extending central axis and in which said side members are yieldably deformable from a first position wherein said members are substantially parallel with said central axis to a second non-parallel position.

11. An apparatus as defined in claim 10 which said locking means further comprises locking member engaging elements formed side members.

12. An apparatus as defined in claim 11 which said locking member of said entry port structure comprises a protuberance extending radially outwardly from said tubular body.

13. An apparatus as defined in claim 11 further including release means for moving said side members to said second unlocked position, said release means comprising spaced apart gripping members connected to said side members.

14. An apparatus as defined in claim 12 which said release means comprise gripping wings integrally formed with said side members and extending therefrom.

15. An apparatus as defined in claim 8 which said septum has a cylindrical body constructed from a resiliently deformable material, said body having a longitudinally extending slit.

16. An apparatus as defined in claim 8 which said cannula comprises a plastic tube having a length sufficient to extend through said septum when said locking means is in engagement with said locking member.

17. An apparatus as defined in claim 8 which said entry port structure comprises a Y site having an outwardly protruding arm.

18. An entry port structure usable with a cannula, comprising:

(a) a tubular body having an inner wall, a centrally disposed fluid passageway and first and second ports in communication with said passageway; and (b) closure means for closing said first port of said tubular body, said closure means comprising:
(i) septum holding means for holding a septum, including a generally ring shaped member telescopically received within said first port, said member having an outer wall and an inner wall defining a chamber;
(ii) a septum disposed within said chamber, said septum having first and second portions and retaining means disposed between said first and second portions for retaining said septum in said chamber, said septum being penetrable by the cannula; and
(iii) locking means for locking said closure means within said first port, said locking means comprising a protuberance formed on one of said outer wall of said generally ring shaped member and said inner wall of said tubular body and a protuberance receiving groove formed on the other of said outer wall of said generally ring shaped member and said inner wall of said tubular body.

19. An entry port structure as defined in claim 18 in which said retaining means comprises a protuberance formed on one of said septum and said ring shaped member and a groove formed on the other of said septum and said ring shaped member.

20. An entry port structure as defined in claim 19 in which said retaining means comprises a generally annular shaped segment integrally formed with said generally ring shaped member.

21. An entry port structure as defined in claim 19 in which said generally ring shaped member comprises first and second portions said first portion defining a first subchamber having a first diameter and said second portion defining a second subchamber having a second diameter.

22. An entry port structure as defined in claim 21 in which said septum includes a first enlarged diameter portion disposed within said first subchamber, a second reduced diameter portion disposed within said second subchamber.

23. An entry port structure usable with a cannula, comprising:

(a) a tubular body having an inner wall, a centrally disposed fluid passageway and first and second ports in communication with said passageway; and (b) closure means for closing said first port of said tubular body, said closure means comprising:
(i) septum holding means for holding a septum, including a generally ring shaped member telescopically received within said first port, said member having an outer wall and an inner wall defining a chamber said inner wall having a septum retaining means;
(ii) a septum disposed within said chamber, said septum having a first diameter portion, a second diameter portion and means disposed intermediate said first and second diameter portions for engagement with said septum retaining means of said ring shaped member; and
(iii) locking means for locking said closure means within said first port, said locking means comprising a protuberance formed on one of said outer wall of said generally ring shaped member and said inner wall of said tubular body and a protuberance receiving cavity formed on the other of said outer wall of said ring shaped member and said inner wall of said tubular body.

24. An entry port structure as defined in claim 23 in which said inner wall of said generally ring shaped member comprises first and second portions of said first portion defining a first subchamber having a first diameter and said second portion defining a second subchamber having a second diameter.

25. An entry port structure as defined in claim 24 in which said first diameter portion of said septum is disposed within said first subchamber and in which said second diameter portion of said septum is disposed within said second chamber.

* * * * *